United States Patent
Johnson et al.

(12)

(10) Patent No.: US 6,379,933 B1
(45) Date of Patent: Apr. 30, 2002

(54) METHOD OF TRANSFERRING AT LEAST TWO SACCHARIDE UNITS WITH A POLYGLYCOSYLTRANSFERASE

(75) Inventors: Karl F. Johnson, Willow Grove; Stephen Roth, Gladwyne; Stephanie L. Buczala, Jenkintown, all of PA (US)

(73) Assignee: Neose Technologies, Inc., Horsham, PA (US)

( * ) Notice: Subject to any disclaimer, the term of this patent is extended or adjusted under 35 U.S.C. 154(b) by 0 days.

(21) Appl. No.: 09/338,943

(22) Filed: Jun. 24, 1999

Related U.S. Application Data

(63) Continuation of application No. 08/478,140, filed on Jun. 7, 1995, now Pat. No. 6,127,153.

(51) Int. Cl.$^7$ ................................................. C12P 19/18
(52) U.S. Cl. ........................... 435/97; 435/72; 435/84; 435/100; 435/101; 435/170; 435/871
(58) Field of Search ............................... 435/97, 72, 84, 435/100, 101, 170, 871

(56) References Cited

U.S. PATENT DOCUMENTS

| | | | |
|---|---|---|---|
| 4,918,009 A | | 4/1990 | Nilsson |
| 4,925,796 A | | 5/1990 | Bergh et al. |
| 5,308,460 A | | 5/1994 | Mazid et al. |
| 5,545,553 A | | 8/1996 | Gotschlich |
| 6,127,153 A | * | 10/2000 | Johnson et al. ............... 435/97 |

OTHER PUBLICATIONS

Yamamoto et al, J. Biol. Chem. 265(31): 19257–19262, 1990.*
ATCC Catalog of Bacteria and Bacteriophages, 17$^{th}$ ed., 1989, p. 150.

Andree and Berliner, 1978, "Glucosyl Transferase Activity of Bovine Galactosyl Transferase", Biochim. Biophys. Acta 544:489–495.

Avigad et al., 1962, "The D–Galactose Oxidase of *Polyporus circinatus*", J. Biol. Chem 237:2736–2743.

Gotschlich, 1994, "Genetic Locus for the Biosynthesis of the Variable Portion of *Neisseria gonorrhoeae* Lipooligosaccharide", J. Exp. Med. 180:2181–2190.

Greenwell et al., 1986, "UDP–N–Acetyl–D–Galactosamine as a Donor Substrate for the Glycosyltransferase Encoded by the B Gene at the Human Blood Group ABO Locus", Carbohydrate Res. 149:149–170.

Greenwell et al., 1979, Blood Group A Synthesising Activity of the Blood Group B Gene Specified α–3–D–Galactosyl Transferase.

Palcic and Hindsgaul, 1991, "flexibility in the Donor Substrate Specificity of β 1,4–Galactosyltransferase: Application in the Synthesis of Complex Carbohydrates", Glycobiol. 1:205–209.

Schram et al., 1977, "The Identity of α–Galactosidase B from Human Liver", Biochim. Biopys. Acta 482:138–144.

Takeya et al., 1993, "Biosynthesis of the Blood Group P Antigen–Like GalAcβ1→3Galβ1→4GlcNAc/Glc Structure: Kinetic Evidence for the Responsibility of N–Acetylglucosaminyl–Transferase", Jpn. J. Med. Sci. Biol. 46:1–15.

\* cited by examiner

*Primary Examiner*—Francisco Prats
(74) *Attorney, Agent, or Firm*—Morgan, Lewis & Bockius, LLP

(57) ABSTRACT

The present invention relates to a method of transferring at least two saccharide units with a polyglycosyltransferase, a polyglycosyltransferase and a gene encoding such a polyglycosyltransferase.

18 Claims, 10 Drawing Sheets

Met Gln Pro Leu Val Ser Val Leu Ile Cys Ala Tyr Asn Val Glu Lys
1               5                   10                  15
Tyr Phe Ala Gln Ser Leu Ala Ala Val Val Asn Gln Thr Trp Arg Asn
                20                  25                  30
Leu Asp Ile Leu Ile Val Asp Asp Gly Ser Thr Asp Gly Thr Leu Ala
            35                  40                  45
Ile Ala Lys Asp Phe Gln Lys Arg Asp Ser Arg Ile Lys Ile Leu Ala
        50                  55                  60
Gln Ala Gln Asn Ser Gly Leu Ile Pro Ser Leu Asn Ile Gly Leu Asp
    65              70                  75                  80
Glu Leu Ala Lys Ser Gly Gly Gly Gly Glu Tyr Ile Ala Arg Thr
                85                  90                  95
Asp Ala Asp Asp Ile Ala Ser Pro Gly Trp Ile Glu Lys Ile Val Gly
            100                 105                 110
Glu Met Glu Lys Asp Arg Ser Ile Ile Ala Met Gly Ala Trp Leu Glu
        115                 120                 125
Val Leu Ser Glu Glu Lys Asp Gly Asn Arg Leu Ala Arg His His Lys
    130                 135                 140
His Gly Lys Ile Trp Lys Lys Pro Thr Arg His Glu Asp Ile Ala Ala
145                 150                 155                 160
Phe Phe Pro Phe Gly Asn Pro Ile His Asn Asn Thr Met Ile Met Arg
                165                 170                 175
Arg Ser Val Ile Asp Gly Gly Leu Arg Tyr Asp Thr Glu Arg Asp Trp
            180                 185                 190
Ala Glu Asp Tyr Gln Phe Trp Tyr Asp Val Ser Lys Leu Gly Arg Leu
        195                 200                 205
Ala Tyr Tyr Pro Glu Ala Leu Val Lys Tyr Arg Leu His Ala Asn Gln
    210                 215                 220
Val Ser Ser Lys His Ser Val Arg Gln His Glu Ile Ala Gln Gly Ile
225                 230                 235                 240
Gln Lys Thr Ala Arg Asn Asp Phe Leu Gln Ser Met Gly Phe Lys Thr
                245                 250                 255
Arg Phe Asp Ser Leu Glu Tyr Arg Gln Thr Lys Ala Ala Ala Tyr Glu
            260                 265                 270
Leu Pro Glu Lys Asp Leu Pro Glu Glu Asp Phe Glu Arg Ala Arg Arg
        275                 280                 285

FIG. 1A

Phe Leu Tyr Gln Cys Phe Lys Arg Thr Asp Thr Pro Pro Ser Gly Ala
    290             295             300
Trp Leu Asp Phe Ala Ala Asp Gly Arg Met Arg Arg Leu Phe Thr Leu
305             310             315             320
Arg Gln Tyr Phe Gly Ile Leu Tyr Arg Leu Ile Lys Asn Arg Arg Gln
            325             330             335
Ala Arg Ser Asp Ser Ala Gly Lys Glu Gln Glu Ile
            340             345

FIG. 1B

| | |
|---|---:|
| CTG CAG GCC GTC GCC GTA TTC AAA CAA CTG CCC GAA GCC GCC GCG CTC<br>Leu Gln Ala Val Ala Val Phe Lys Gln Leu Pro Glu Ala Ala Ala Leu<br>1                    5                  10               15 | 48 |
| GCC GCC GCC AAC AAA CGC GTG CAA AAC CTG CTG AAA AAA GCC GAT GCC<br>Ala Ala Ala Asn Lys Arg Val Gln Asn Leu Leu Lys Lys Ala Asp Ala<br>                20                  25                 30 | 96 |
| GCG TTG GGC GAA GTC AAT GAA AGC CTG CTG CAA CAG GAC GAA GAA AAA<br>Ala Leu Gly Glu Val Asn Glu Ser Leu Leu Gln Gln Asp Glu Glu Lys<br>      35                  40                  45 | 144 |
| GCC CTG TAC GCT GCC GCG CAA GGT TTG CAG CCG AAA ATT GCC GCC GCC<br>Ala Leu Tyr Ala Ala Ala Gln Gly Leu Gln Pro Lys Ile Ala Ala Ala<br>    50                  55                  60 | 192 |
| GTC GCC GAA GGC AAT TTC CGA ACC GCC TTG TCC GAA CTG GCT TCC GTC<br>Val Ala Glu Gly Asn Phe Arg Thr Ala Leu Ser Glu Leu Ala Ser Val<br>65                  70                  75               80 | 240 |
| AAG CCG CAG GTT GAT GCC TTC TTC GAC GGC GTG ATG GTG ATG GCG GAA<br>Lys Pro Gln Val Asp Ala Phe Phe Asp Gly Val Met Val Met Ala Glu<br>                85                  90                 95 | 288 |
| GAT GCC GCC GTA AAA CAA AAC CGC CTG AAC CTG CTG AAC CGC TTG GCA<br>Asp Ala Ala Val Lys Gln Asn Arg Leu Asn Leu Leu Asn Arg Leu Ala<br>           100                 105               110 | 336 |
| GAG CAG ATG AAC GCG GTG GCC GAC ATC GCG CTT TTG GGC GAG TAA<br>Glu Gln Met Asn Ala Val Ala Asp Ile Ala Leu Leu Gly Glu<br>           115                 120               125 | 381 |
| CCGTTGTACA GTCCAAATGC CGTCTGAAGC CTTCAGGCGG CATCAAATTA TCGGGAGAGT | 441 |
| AAA TTG CAG CCT TTA GTC AGC GTA TTG ATT TGC GCC TAC AAC GTA GAA<br>    Met Gln Pro Leu Val Ser Val Leu Ile Cys Ala Tyr Asn Val Glu<br>       1                 5                  10               15 | 489 |
| AAA TAT TTT GCC CAA TCA TTA GCC GCC GTC GTG AAT CAG ACT TGG CGC<br>Lys Tyr Phe Ala Gln Ser Leu Ala Ala Val Val Asn Gln Thr Trp Arg<br>                20                  25                 30 | 537 |
| AAC TTG GAT ATT TTG ATT GTC GAT GAC GGC TCG ACA GAC GGC ACA CTT<br>Asn Leu Asp Ile Leu Ile Val Asp Asp Gly Ser Thr Asp Gly Thr Leu<br>                35                  40                 45 | 585 |
| GCC ATT GCC AAG GAT TTT CAA AAG CGG GAC AGC CGT ATC AAA ATC CTT<br>Ala Ile Ala Lys Asp Phe Gln Lys Arg Asp Ser Arg Ile Lys Ile Leu<br>    50                  55                  60 | 633 |
| GCA CAA GCT CAA AAT TCC GGC CTG ATT CCC TCT TTA AAC ATC GGG CTG<br>Ala Gln Ala Gln Asn Ser Gly Leu Ile Pro Ser Leu Asn Ile Gly Leu<br>65                  70                  75 | 681 |
| GAC GAA TTG GCA AAG TCG GGG GGG GGG GGG GAA TAT ATT GCG CGC<br>Asp Glu Leu Ala Lys Ser Gly Gly Gly Gly Gly Glu Tyr Ile Ala Arg<br>80                  85                  90               95 | 729 |

FIG. 2A

```
ACC GAT GCC GAC GAT ATT GCC TCC CCC GGC TGG ATT GAG AAA ATC GTG    777
Thr Asp Ala Asp Asp Ile Ala Ser Pro Gly Trp Ile Glu Lys Ile Val
            100                 105                 110
GGC GAG ATG GAA AAA GAC CGC AGC ATC ATT GCG ATG GGC GCG TGG CTG    825
Gly Glu Met Glu Lys Asp Arg Ser Ile Ile Ala Met Gly Ala Trp Leu
            115                 120                 125
GAA GTT TTG TCG GAA GAA AAG GAC GGC AAC CGG CTG GCG CGG CAC CAC    873
Glu Val Leu Ser Glu Glu Lys Asp Gly Asn Arg Leu Ala Arg His His
            130                 135                 140
AAA CAC GGC AAA ATT TGG AAA AAG CCG ACC CGG CAC GAA GAC ATC GCC    921
Lys His Gly Lys Ile Trp Lys Lys Pro Thr Arg His Glu Asp Ile Ala
    145                 150                 155
GCC TTT TTC CCT TTC GGC AAC CCC ATA CAC AAC AAC ACG ATG ATT ATG    969
Ala Phe Phe Pro Phe Gly Asn Pro Ile His Asn Asn Thr Met Ile Met
160                 165                 170                 175
CGG CGC AGC GTC ATT GAC GGC GGT TTG CGT TAC GAC ACC GAG CGG GAT   1017
Arg Arg Ser Val Ile Asp Gly Gly Leu Arg Tyr Asp Thr Glu Arg Asp
                180                 185                 190
TGG GCG GAA GAT TAC CAA TTT TGG TAC GAT GTC AGC AAA TTG GGC AGG   1065
Trp Ala Glu Asp Tyr Gln Phe Trp Tyr Asp Val Ser Lys Leu Gly Arg
                195                 200                 205
CTG GCT TAT TAT CCC GAA GCC TTG GTC AAA TAC CGC CTT CAC GCC AAT   1113
Leu Ala Tyr Tyr Pro Glu Ala Leu Val Lys Tyr Arg Leu His Ala Asn
            210                 215                 220
CAG GTT TCA TCC AAA CAC AGC GTC CGC CAA CAC GAA ATC GCG CAA GGC   1161
Gln Val Ser Ser Lys His Ser Val Arg Gln His Glu Ile Ala Gln Gly
            225                 230                 235
ATC CAA AAA ACC GCC AGA AAC GAT TTT TTG CAG TCT ATG GGT TTT AAA   1209
Ile Gln Lys Thr Ala Arg Asn Asp Phe Leu Gln Ser Met Gly Phe Lys
240                 245                 250                 255
ACC CGG TTC GAC AGC CTA GAA TAC CGC CAA ACA AAA GCA GCG GCG TAT   1257
Thr Arg Phe Asp Ser Leu Glu Tyr Arg Gln Thr Lys Ala Ala Ala Tyr
                260                 265                 270
GAA CTG CCG GAG AAG GAT TTG CCG GAA GAA GAT TTT GAA CGC GCC CGC   1305
Glu Leu Pro Glu Lys Asp Leu Pro Glu Glu Asp Phe Glu Arg Ala Arg
                275                 280                 285
CGG TTT TTG TAC CAA TGC TTC AAA CGG ACG GAC ACG CCG CCC TCC GGC   1353
Arg Phe Leu Tyr Gln Cys Phe Lys Arg Thr Asp Thr Pro Pro Ser Gly
            290                 295                 300
GCG TGG CTG GAT TTC GCG GCA GAC GGC AGG ATG AGG CGG CTG TTT ACC   1401
Ala Trp Leu Asp Phe Ala Ala Asp Gly Arg Met Arg Arg Leu Phe Thr
    305                 310                 315
```

FIG. 2B

```
TTG AGG CAA TAC TTC GGC ATT TTG TAC CGG CTG ATT AAA AAC CGC CGG   1449
Leu Arg Gln Tyr Phe Gly Ile Leu Tyr Arg Leu Ile Lys Asn Arg Arg
320             325                 330                 335
CAG GCG CGG TCG GAT TCG GCA GGG AAA GAA CAG GAG ATT TAA           1491
Gln Ala Arg Ser Asp Ser Ala Gly Lys Glu Gln Glu Ile
                340                 345
TGCAAAACCA CGTTATCAGC TTGGCTTCCG CCGCAGAACG CAGGGCGCAC ATTGCCGCAA 1551

CCTTCGGCAG TCGCGGCATC CCGTTCCAGT TTTTCGACGC ACTGATGCCG TCTGAAAGGC 1611

TGGAACGGGC AATGGCGGAA CTCGTCCCCG GCTTGTCGGC GCACCCCTAT TTGAGCGGAG 1671

TGGAAAAAGC CTGCTTTATG AGCCACGCCG TATTGTGGGA ACAGGCATTG ACGAAGGCG  1731

TACCGTATAT CGCCGTATTT GAAGATGATG TCTTACTCGG CGAAGGCGCG GAGCAGTTCC 1791

TTGCCGAAGA TACTTGGCTG CAAGAACGCT TTGACCCCGA TTCCGCCTTT GTCGTCCGCT 1851

TGGAAACGAT GTTTATGCAC GTCCTGACCT CGCCCTCCGG CGTGGCGGAC TACGGCGGGC 1911

GCGCCTTTCC GCTTTTGGAA AGCGAACACT GCGGGACGGC GGGCTATATT ATTTCCCGAA 1971

AGGCGATGCG TTTTTTCTTG ACAGGTTTG CCGTTTTGCC GCCCGAACGC CTGCACCCTG  2031

TCGATTTGAT GATGTTCGGC AACCCTGACG ACAGGGAAGG AATGCCGGTT TGCCAGCTCA 2091

ATCCCGCCTT GTGCGCCCAA GAGCTGCATT ATGCCAAGTT TCACGACCAA AACAGCGCAT 2151

TGGGCAGCCT GATCGAACAT GACCGCCGCC TGAACCGCAA ACAGCAATGG CGCGATTCCC 2211

CCGCCAACAC ATTCAAACAC CGCCTGATCC GCGCCTTGAC CAAAATCGGC AGGGAAAGGG 2271

AAAAACGCCG GCAAAGGCGC GAACAGTTAA TCGGCAAGAT TATTGTGCCT TTCCAATAAA 2331

AGGAGAAAAG ATG GAC ATC GTA TTT GCG GCA GAC GAC AAC TAT GCC GCC-  2380
           Met Asp Ile Val Phe Ala Ala Asp Asp Asn Tyr Ala Ala
            1               5                   10
TAC CTT TGC GTT GCG GCA AAA AGC GTG GAA GCG GCC CAT CCC GAT ACG   2428
Tyr Leu Cys Val Ala Ala Lys Ser Val Glu Ala Ala His Pro Asp Thr
        15              20                  25
GAA ATC AGG TTC CAC GTC CTC GAT GCC GGC ATC AGT GAG GAA AAC CGG   2476
Glu Ile Arg Phe His Val Leu Asp Ala Gly Ile Ser Glu Glu Asn Arg
    30              35                  40                  45
```

FIG. 2C

```
GCG GCG GTT GCC GCC AAT TTG CGG GGG GGG GGT AAT ATC CGC TTT ATA 2524
Ala Ala Val Ala Ala Asn Leu Arg Gly Gly Gly Asn Ile Arg Phe Ile
            50                      55                      60
GAC GTA AAC CCC GAA GAT TTC GCC GGC TTC CCC TTA AAC ATC AGG CAC 2572
Asp Val Asn Pro Glu Asp Phe Ala Gly Phe Pro Leu Asn Ile Arg His
            65                      70                      75
ATT TCC ATT ACG ACT TAT GCC CGC CTG AAA TTG GGC GAA TAC ATT GCC 2620
Ile Ser Ile Thr Thr Tyr Ala Arg Leu Lys Leu Gly Glu Tyr Ile Ala
            80                      85                      90
GAT TGC GAC AAA GTC CTG TAT CTG GAT ACG GAC GTA TTG GTC AGG GAC 2668
Asp Cys Asp Lys Val Leu Tyr Leu Asp Thr Asp Val Leu Val Arg Asp
            95                      100                     105
GGC CTG AAG CCC TTA TGG GAT ACC GAT TTG GGC GGT AAC TGG GTC GGC 2716
Gly Leu Lys Pro Leu Trp Asp Thr Asp Leu Gly Gly Asn Trp Val Gly
110                     115                     120                 125
GCG TGC ATC GAT TTG TTT GTC GAA AGG CAG GAA GGA TAC AAA CAA AAA 2764
Ala Cys Ile Asp Leu Phe Val Glu Arg Gln Glu Gly Tyr Lys Gln Lys
            130                     135                     140
ATC GGT ATG GCG GAC GGA GAA TAT TAT TTC AAT GCC GGC GTA TTG CTG 2812
Ile Gly Met Ala Asp Gly Glu Tyr Tyr Phe Asn Ala Gly Val Leu Leu
            145                     150                     155
ATC AAC CTG AAA AAG TGG CGG CGG CAC GAT ATT TTC AAA ATG TCC TGC 2860
Ile Asn Leu Lys Lys Trp Arg Arg His Asp Ile Phe Lys Met Ser Cys
            160                     165                     170
GAA TGG GTG GAA CAA TAC AAG GAC GTG ATG CAA TAT CAG GAT CAG GAC 2908
Glu Trp Val Glu Gln Tyr Lys Asp Val Met Gln Tyr Gln Asp Gln Asp
            175                     180                     185
ATT TTG AAC GGG CTG TTT AAA GGC GGG GTG TGT TAT GCG AAC AGC CGT 2956
Ile Leu Asn Gly Leu Phe Lys Gly Gly Val Cys Tyr Ala Asn Ser Arg
190                     195                     200                 205
TTC AAC TTT ATG CCG ACC AAT TAT GCC TTT ATG GCG AAC GGG TTT GCG 3004
Phe Asn Phe Met Pro Thr Asn Tyr Ala Phe Met Ala Asn Gly Phe Ala
            210                     215                     220
TCC CGC CAT ACC GAC CCG CTT TAC CTC GAC CGT ACC AAT ACG GCG ATG 3052
Ser Arg His Thr Asp Pro Leu Tyr Leu Asp Arg Thr Asn Thr Ala Met
            225                     230                     235
CCC GTC GCC GTC AGC CAT TAT TGC GGC TCG GCA AAG CCG TGG CAC AGG 3100
Pro Val Ala Val Ser His Tyr Cys Gly Ser Ala Lys Pro Trp His Arg
            240                     245                     250
GAC TGC ACC GTT TGG GGT GCG GAA CGT TTC ACA GAG TTG GCC GGC AGC 3148
Asp Cys Thr Val Trp Gly Ala Glu Arg Phe Thr Glu Leu Ala Gly Ser
            255                     260                     265
```

FIG. 2D

```
CTG ACG ACC GTT CCC GAA GAA TGG CGC GGC AAA CTT GCC GTC CCG CCG   3196
Leu Thr Thr Val Pro Glu Glu Trp Arg Gly Lys Leu Ala Val Pro Pro
270             275             280             285
ACA AAG TGT ATG CTT CAA AGA TGG CGC AAA AAG CTG TCT GCC AGA TTC   3244
Thr Lys Cys Met Leu Gln Arg Trp Arg Lys Lys Leu Ser Ala Arg Phe
            290             295             300
TTA CGC AAG ATT TAT TGA CGGGGCAGGC CGTCTGAAGC CTTCAGACGG          3292
Leu Arg Lys Ile Tyr
            305
CATCGGACGT ATCGGAAAGG AGAAACGGA TTG CAG CCT TTA GTC AGC GTA TTG   3345
                                Met Gln Pro Leu Val Ser Val Leu
                                  1              5
ATT TGC GCC TAC AAC GCA GAA AAA TAT TTT GCC CAA TCA TTG GCC GCC   3393
Ile Cys Ala Tyr Asn Ala Glu Lys Tyr Phe Ala Gln Ser Leu Ala Ala
        10              15              20
GTA GTG GGG CAG ACT TGG CGC AAC TTG GAT ATT TTG ATT GTC GAT GAC   3441
Val Val Gly Gln Thr Trp Arg Asn Leu Asp Ile Leu Ile Val Asp Asp
25              30              35              40
GGC TCG ACG GAC GGC ACG CCC GCC ATT GCC CGG CAT TTC CAA GAA CAG   3489
Gly Ser Thr Asp Gly Thr Pro Ala Ile Ala Arg His Phe Gln Glu Gln
                45              50              55
GAC GGC AGG ATC AGG ATA ATT TCC AAT CCC CGC AAT TTG GGC TTT ATC   3537
Asp Gly Arg Ile Arg Ile Ile Ser Asn Pro Arg Asn Leu Gly Phe Ile
                60              65              70
GCC TCT TTA AAC ATC GGG CTG GAC GAA TTG GCA AAG TCG GGG GGG GGG   3585
Ala Ser Leu Asn Ile Gly Leu Asp Glu Leu Ala Lys Ser Gly Gly Gly
        75              80              85
GAA TAT ATT GCG CGC ACC GAT GCC GAC GAT ATT GCC TCC CCC GGC TGG   3633
Glu Tyr Ile Ala Arg Thr Asp Ala Asp Asp Ile Ala Ser Pro Gly Trp
90              95              100
ATT GAG AAA ATC GTG GGC GAG ATG GAA AAA GAC CGC AGC ATC ATT GCG   3681
Ile Glu Lys Ile Val Gly Glu Met Glu Lys Asp Arg Ser Ile Ile Ala
105             110             115             120
ATG GGC GCG TGG TTG GAA GTT TTG TCG GAA GAA AAC AAT AAA AGC GTG   3729
Met Gly Ala Trp Leu Glu Val Leu Ser Glu Glu Asn Asn Lys Ser Val
                125             130             135
CTT GCC GCC ATT GCC CGA AAC GGC GCA ATT TGG GAC AAA CCG ACC CGG   3777
Leu Ala Ala Ile Ala Arg Asn Gly Ala Ile Trp Asp Lys Pro Thr Arg
                140             145             150
CAT GAA GAC ATT GTC GCC GTT TTC CCT TTC GGC AAC CCC ATA CAC AAC   3825
His Glu Asp Ile Val Ala Val Phe Pro Phe Gly Asn Pro Ile His Asn
            155             160             165
```

FIG. 2E

```
AAC ACG ATG ATT ATG AGG CGC AGC GTC ATT GAC GGC GGT TTG CGG TTC   3873
Asn Thr Met Ile Met Arg Arg Ser Val Ile Asp Gly Gly Leu Arg Phe
        170             175             180
GAT CCA GCC TAT ATC CAC GCC GAA GAC TAT AAG TTT TGG TAC GAA GCC   3921
Asp Pro Ala Tyr Ile His Ala Glu Asp Tyr Lys Phe Trp Tyr Glu Ala
185             190             195             200
GGC AAA CTG GGC AGG CTG GCT TAT TAT CCC GAA GCC TTG GTC AAA TAC   3969
Gly Lys Leu Gly Arg Leu Ala Tyr Tyr Pro Glu Ala Leu Val Lys Tyr
                205             210             215
CGC TTC CAT CAA GAC CAG ACT TCT TCC AAA TAC AAC CTG CAA CAG CGC   4017
Arg Phe His Gln Asp Gln Thr Ser Ser Lys Tyr Asn Leu Gln Gln Arg
        220             225             230
AGG ACG GCG TGG AAA ATC AAA GAA GAA ATC AGG GCG GGG TAT TGG AAG   4065
Arg Thr Ala Trp Lys Ile Lys Glu Glu Ile Arg Ala Gly Tyr Trp Lys
        235             240             245
GCG GCA GGC ATA GCC GTC GGG GCG GAC TGC CTG AAT TAC GGG CTT TTG   4113
Ala Ala Gly Ile Ala Val Gly Ala Asp Cys Leu Asn Tyr Gly Leu Leu
250             255             260
AAA TCA ACG GCA TAT GCG TTG TAC GAA AAA GCC TTG TCC GGA CAG GAT   4161
Lys Ser Thr Ala Tyr Ala Leu Tyr Glu Lys Ala Leu Ser Gly Gln Asp
265             270             275             280
ATC GGA TGC CTC CGC CTG TTC CTG TAC GAA TAT TTC TTG TCG TTG GAA   4209
Ile Gly Cys Leu Arg Leu Phe Leu Tyr Glu Tyr Phe Leu Ser Leu Glu
                285             290             295
AAG TAT TCT TTG ACC GAT TTG CTG GAT TTC TTG ACA GAC CGC GTG ATG   4257
Lys Tyr Ser Leu Thr Asp Leu Leu Asp Phe Leu Thr Asp Arg Val Met
                300             305             310
AGG AAG CTG TTT GCC GCA CCG CAA TAT AGG AAA ATC CTG AAA AAA ATG   4305
Arg Lys Leu Phe Ala Ala Pro Gln Tyr Arg Lys Ile Leu Lys Lys Met
        315             320             325
TTA CGC CCT TGG AAA TAC CGC AGC TAT TGA AACCGAACAG GATAAATC ATG   4356
Leu Arg Pro Trp Lys Tyr Arg Ser Tyr                          Met
        330             335                                    1
CAA AAC CAC GTT ATC AGC TTG GCT TCC GCC GCA GAG CGC AGG GCG CAC   4404
Gln Asn His Val Ile Ser Leu Ala Ser Ala Ala Glu Arg Arg Ala His
            5               10              15
ATT GCC GAT ACC TTC GGC AGT CGC GGC ATC CCG TTC CAG TTT TTC GAC   4452
Ile Ala Asp Thr Phe Gly Ser Arg Gly Ile Pro Phe Gln Phe Phe Asp
        20              25              30
GCA CTG ATG CCG TCT GAA AGG CTG GAA CAG GCG ATG GCG GAA CTC GTC   4500
Ala Leu Met Pro Ser Glu Arg Leu Glu Gln Ala Met Ala Glu Leu Val
35              40              45
```

FIG. 2F

```
CCC GGC TTG TCG GCG CAC CCC TAT TTG AGC GGA GTG GAA AAA GCC TGC  4548
Pro Gly Leu Ser Ala His Pro Tyr Leu Ser Gly Val Glu Lys Ala Cys
 50              55                  60                  65
TTT ATG AGC CAC GCC GTA TTG TGG GAA CAG GCG TTG GAT GAA GGT CTG  4596
Phe Met Ser His Ala Val Leu Trp Glu Gln Ala Leu Asp Glu Gly Leu
                 70                  75                  80
CCG TAT ATC GCC GTA TTT GAG GAC GAC GTT TTA CTC GGC GAA GGC GCG  4644
Pro Tyr Ile Ala Val Phe Glu Asp Asp Val Leu Leu Gly Glu Gly Ala
             85                  90                  95
GAG CAG TTC CTT GCC GAA GAT ACT TGG TTG GAA GAG CGT TTT GAC AAG  4692
Glu Gln Phe Leu Ala Glu Asp Thr Trp Leu Glu Glu Arg Phe Asp Lys
            100                 105                 110
GAT TCC GCC TTT ATC GTC CGT TTG GAA ACG ATG TTT GCG AAA GTT ATT  4740
Asp Ser Ala Phe Ile Val Arg Leu Glu Thr Met Phe Ala Lys Val Ile
        115                 120                 125
GTC AGA CCG GAT AAA GTC CTG AAT TAT GAA AAC CGG TCA TTT CCT TTG  4788
Val Arg Pro Asp Lys Val Leu Asn Tyr Glu Asn Arg Ser Phe Pro Leu
130                 135                 140                 145
CTG GAG AGC GAA CAT TGT GGG ACG GCT GGC TAT ATC ATT TCG CGT GAG  4836
Leu Glu Ser Glu His Cys Gly Thr Ala Gly Tyr Ile Ile Ser Arg Glu
                150                 155                 160
GCG ATG CGG TTT TTC TTG GAC AGG TTT GCC GTT TTG CCG CCA GAG CGG  4SS4
Ala Met Arg Phe Phe Leu Asp Arg Phe Ala Val Leu Pro Pro Glu Arg
            165                 170                 175
ATT AAA GCG GTA GAT TTG ATG ATG TTT ACT TAT TTC TTT GAT AAG GAG  4932
Ile Lys Ala Val Asp Leu Met Met Phe Thr Tyr Phe Phe Asp Lys Glu
        180                 185                 190
GGG ATG CCT GTT TAT CAG GTT AGT CCC GCC TTA TGT ACC CAA GAA TTG  4980
Gly Met Pro Val Tyr Gln Val Ser Pro Ala Leu Cys Thr Gln Glu Leu
195                 200                 205
CAT TAT GCC AAG TTT CTC AGT CAA AAC AGT ATG TTG GGT AGC GAT TTG  5028
His Tyr Ala Lys Phe Leu Ser Gln Asn Ser Met Leu Gly Ser Asp Leu
210                 215                 220                 225
GAA AAA GAT AGG GAA CAA GGA AGA AGA CAC CGC CGT TCG TTG AAG GTG  5076
Glu Lys Asp Arg Glu Gln Gly Arg Arg His Arg Arg Ser Leu Lys Val
                230                 235                 240
ATG TTT GAC TTG AAG CGT GCT TTG GGT AAA TTC GGT AGG GAA AAG AAG  5124
Met Phe Asp Leu Lys Arg Ala Leu Gly Lys Phe Gly Arg Glu Lys Lys
            245                 250                 255
AAA AGA ATG GAG CGT CAA AGG CAG GCG GAG CTT GAG AAA GTT TAC GGC  5172
Lys Arg Met Glu Arg Gln Arg Gln Ala Glu Leu Glu Lys Val Tyr Gly
        260                 265                 270
```

FIG. 2G

```
AGG CGG GTC ATA TTG TTC AAA TAG TTTGTGTAAA ATATAGGGGA TTAAAATCAG 5226
Arg Arg Val Ile Leu Phe Lys
      275                 280
AAATGGACAC ACTGTCATTC CGCGCAGGC GGGAATCTAG GTCTTTAAAC TTCGGTTTTT 5286

TCCGATAAAT TCTTGCCGCA TTAAAATTCC AGATTCCCGC TTTCGCGGGG ATGACGGCGG 5346

GGGGATTGTT GCTTTTTCGG ATAAAATCCC GTGTTTTTTC ATCTGCTAGG TAAAATCGCC 5406

CCAAAGCGTC TGCATCGCGG CGATGGCGGC GAGTGGGGCG GTTTCTGTGC GTAAAATCCG 5466

TTTTCCGAGT GTAACCGCCT GAAAGCCGGC TTCAAATGCC TGTTGTTCTT CCTGTTCTGT 5526

CCAGCCGCCT TCGGGCCCGA CCATAAAGAC GATTGCGCCG GACGGGTGGC GGATGTCGCC 5586

GAGTTTGCAG GCGCGGTTGA TGCTCATAAT CAGCTTGGTG TTTTCAGACG GCATTTTGTC 5646

GAGTGCTTCA CGGTAGCCGA TGATGGGCAG TACGGGGGGA ACGGTGTTCC TGCCGCTTTG 5706

TTCGCACGCG GAGATGACGA TTTCCTGCCA GCGTGCGAGG CGTTTGGCGG CGCGTTCTCC 5766

GTCGAGGCGG ACGATGCAGC GTTCGCTGAT GACGGGCTGT ATGGCGGTTA CGCCGAGTTC 5826

GACGCTTTTT TGCAGGGTGA AATCCATGCG ATC                              5859
```

FIG. 2H

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 5859 base pairs
        (B) TYPE: nucleic acid
        (C) STRANDEDNESS: single
        (D) TOPOLOGY: linear (ii) MOLECULE TYPE:

(iv) ANTI-SENSE: NO (vi) ORIGINAL SOURCE:
        (B) STRAIN: F62

(ix) FEATURE:
        (A) NAME/KEY: CDS
        (B) LOCATION: 1..381

(ix) FEATURE:
        (A) NAME/KEY: CDS
        (B) LOCATION: 445..1491

(ix) FEATURE:
        (A) NAME/KEY: CDS
        (B) LOCATION: 2342..3262

(ix) FEATURE:
        (A) NAME/KEY: CDS
        (B) LOCATION: 3322..4335

(ix) FEATURE:
        (A) NAME/KEY: CDS
        (B) LOCATION: 4354..5196

(xi) SEQUENCE DESCRIPTION: SEQ ID NO:1:

```
CTG CAG GCC GTC GCC GTA TTC AAA CAA CTG CCC GAA GCC GCC GCG CTC      48
Leu Gln Ala Val Ala Val Phe Lys Gln Leu Pro Glu Ala Ala Ala Leu
 1               5                  10                  15

GCC GCC GCC AAC AAA CGC GTG CAA AAC CTG CTG AAA AAA GCC GAT GCC      96
Ala Ala Ala Asn Lys Arg Val Gln Asn Leu Leu Lys Lys Ala Asp Ala
                20                  25                  30

GCG TTG GGC GAA GTC AAT GAA AGC CTG CTG CAA CAG GAC GAA GAA AAA     144
Ala Leu Gly Glu Val Asn Glu Ser Leu Leu Gln Gln Asp Glu Glu Lys
            35                  40                  45

GCC CTG TAC GCT GCC GCG CAA GGT TTG CAG CCG AAA ATT GCC GCC GCC     192
Ala Leu Tyr Ala Ala Ala Gln Gly Leu Gln Pro Lys Ile Ala Ala Ala
         50                  55                  60

GTC GCC GAA GGC AAT TTC CGA ACC GCC TTG TCC GAA CTG GCT TCC GTC     240
Val Ala Glu Gly Asn Phe Arg Thr Ala Leu Ser Glu Leu Ala Ser Val
 65                  70                  75                  80

AAG CCG CAG GTT GAT GCC TTC TTC GAC GGC GTG ATG GTG ATG GCG GAA     288
Lys Pro Gln Val Asp Ala Phe Phe Asp Gly Val Met Val Met Ala Glu
                 85                  90                  95

GAT GCC GCC GTA AAA CAA AAC CGC CTG AAC CTG CTG AAC CGC TTG GCA     336
Asp Ala Ala Val Lys Gln Asn Arg Leu Asn Leu Leu Asn Arg Leu Ala
                100                 105                 110

GAG CAG ATG AAC GCG GTG GCC GAC ATC GCG CTT TTG GGC GAG TAA         381
Glu Gln Met Asn Ala Val Ala Asp Ile Ala Leu Leu Gly Glu
            115                 120                 125

CCGTTGTACA GTCCAAATGC CGTCTGAAGC CTTCAGGCGG CATCAAATTA TCGGGAGAGT   441
```

```
AAA TTG CAG CCT TTA GTC AGC GTA TTA ATT TGC GCC TAC AAC GTA GAA        489
Lys Leu Gln Pro Leu Val Ser Val Leu Ile Cys Ala Tyr Asn Val Glu
  1               5                  10                  15

AAA TAT TTT GCC CAA TCA TTA GCC GCC GTC GTG AAT CAG ACT TGG CGC        537
Lys Tyr Phe Ala Gln Ser Leu Ala Ala Val Val Asn Gln Thr Trp Arg
             20                  25                  30

AAC TTG GAT ATT TTG ATT GTC GAT GAC GGC TCG ACA GAC GGC ACA CTT        585
Asn Leu Asp Ile Leu Ile Val Asp Asp Gly Ser Thr Asp Gly Thr Leu
                 35                  40                  45

GCC ATT GCC AAG GAT TTT CAA AAG CGG GAC AGC CGT ATC AAA ATC CTT        633
Ala Ile Ala Lys Asp Phe Gln Lys Arg Asp Ser Arg Ile Lys Ile Leu
             50                  55                  60

GCA CAA GCT CAA AAT TCC GGC CTG ATT CCC TCT TTA AAC ATC GGG CTG        681
Ala Gln Ala Gln Asn Ser Gly Leu Ile Pro Ser Leu Asn Ile Gly Leu
 65                  70                  75

GAC GAA TTG GCA AAG TCG GGG GGG GGG GGG GAA TAT ATT GCG CGC            729
Asp Glu Leu Ala Lys Ser Gly Gly Gly Gly Glu Tyr Ile Ala Arg
 80                  85                  90                  95

ACC GAT GCC GAC GAT ATT GCC TCC CCC GGC TGG ATT GAG AAA ATC GTG        777
Thr Asp Ala Asp Asp Ile Ala Ser Pro Gly Trp Ile Glu Lys Ile Val
                100                 105                 110

GGC GAG ATG GAA AAA GAC CGC AGC ATC ATT GCG ATG GGC GCG TGG CTG        825
Gly Glu Met Glu Lys Asp Arg Ser Ile Ile Ala Met Gly Ala Trp Leu
            115                 120                 125

GAA GTT TTG TCG GAA GAA AAG GAC GGC AAC CGG CTG GCG CGG CAC CAC        873
Glu Val Leu Ser Glu Glu Lys Asp Gly Asn Arg Leu Ala Arg His His
            130                 135                 140

AAA CAC GGC AAA ATT TGG AAA AAG CCG ACC CGG CAC GAA GAC ATC GCC        921
Lys His Gly Lys Ile Trp Lys Lys Pro Thr Arg His Glu Asp Ile Ala
145                 150                 155

GCC TTT TTC CCT TTC GGC AAC CCC ATA CAC AAC AAC ACG ATG ATT ATG        969
Ala Phe Phe Pro Phe Gly Asn Pro Ile His Asn Asn Thr Met Ile Met
160                 165                 170                 175

CGG CGC AGC GTC ATT GAC GGC GGT TTG CGT TAC GAC ACC GAG CGG GAT       1017
Arg Arg Ser Val Ile Asp Gly Gly Leu Arg Tyr Asp Thr Glu Arg Asp
                180                 185                 190

TGG GCG GAA GAT TAC CAA TTT TGG TAC GAT GTC AGC AAA TTG GGC AGG       1065
Trp Ala Glu Asp Tyr Gln Phe Trp Tyr Asp Val Ser Lys Leu Gly Arg
            195                 200                 205

CTG GCT TAT TAT CCC GAA GCC TTG GTC AAA TAC CGC CTT CAC GCC AAT       1113
Leu Ala Tyr Tyr Pro Glu Ala Leu Val Lys Tyr Arg Leu His Ala Asn
            210                 215                 220

CAG GTT TCA TCC AAA CAC AGC GTC CGC CAA CAC GAA ATC GCG CAA GGC       1161
Gln Val Ser Ser Lys His Ser Val Arg Gln His Glu Ile Ala Gln Gly
225                 230                 235

ATC CAA AAA ACC GCC AGA AAC GAT TTT TTG CAG TCT ATG GGT TTT AAA       1209
Ile Gln Lys Thr Ala Arg Asn Asp Phe Leu Gln Ser Met Gly Phe Lys
240                 245                 250                 255

ACC CGG TTC GAC AGC CTA GAA TAC CGC CAA ACA AAA GCA GCG GCG TAT       1257
Thr Arg Phe Asp Ser Leu Glu Tyr Arg Gln Thr Lys Ala Ala Ala Tyr
                260                 265                 270

GAA CTG CCG GAG AAG GAT TTG CCG GAA GAA GAT TTT GAA CGC GCC CGC       1305
Glu Leu Pro Glu Lys Asp Leu Pro Glu Glu Asp Phe Glu Arg Ala Arg
            275                 280                 285

CGG TTT TTG TAC CAA TGC TTC AAA CGG ACG GAC ACG CCG CCC TCC GGC       1353
Arg Phe Leu Tyr Gln Cys Phe Lys Arg Thr Asp Thr Pro Pro Ser Gly
            290                 295                 300

GCG TGG CTG GAT TTC GCG GCA GAC GGC AGG ATG AGG CGG CTG TTT ACC       1401
Ala Trp Leu Asp Phe Ala Ala Asp Gly Arg Met Arg Arg Leu Phe Thr
305                 310                 315
```

-continued

```
TTG AGG CAA TAC TTC GGC ATT TTG TAC CGG CTG ATT AAA AAC CGC CGG    1449
Leu Arg Gln Tyr Phe Gly Ile Leu Tyr Arg Leu Ile Lys Asn Arg Arg
320                 325                 330                 335

CAG GCG CGG TCG GAT TCG GCA GGG AAA GAA CAG GAG ATT TAA            1491
Gln Ala Arg Ser Asp Ser Ala Gly Lys Glu Gln Glu Ile
                340                 345

TGCAAAACCA CGTTATCAGC TTGGCTTCCG CCGCAGAACG CAGGGCGCAC ATTGCCGCAA  1551

CCTTCGGCAG TCGCGGCATC CCGTTCCAGT TTTTCGACGC ACTGATGCCG TCTGAAAGGC  1611

TGGAACGGGC AATGGCGGAA CTCGTCCCCG GCTTGTCGGC GCACCCCTAT TTGAGCGGAG  1671

TGGAAAAAGC CTGCTTTATG AGCCACGCCG TATTGTGGGA ACAGGCATTG ACGAAGGCG   1731

TACCGTATAT CGCCGTATTT GAAGATGATG TCTTACTCGG CGAAGGCGCG GAGCAGTTCC  1791

TTGCCGAAGA TACTTGGCTG CAAGAACGCT TTGACCCCGA TTCCGCCTTT GTCGTCCGCT  1851

TGGAAACGAT GTTTATGCAC GTCCTGACCT CGCCCTCCGG CGTGGCGGAC TACGGCGGGC  1911

GCGCCTTTCC GCTTTTGGAA AGCGAACACT GCGGGACGGC GGGCTATATT ATTTCCCGAA  1971

AGGCGATGCG TTTTTTCTTG ACAGGTTTG CCGTTTTGCC GCCCGAACGC CTGCACCCTG   2031

TCGATTTGAT GATGTTCGGC AACCCTGACG ACAGGGAAGG AATGCCGGTT TGCCAGCTCA  2091

ATCCCGCCTT GTGCGCCCAA GAGCTGCATT ATGCCAAGTT TCACGACCAA ACAGCGCAT   2151

TGGGCAGCCT GATCGAACAT GACCGCCGCC TGAACCGCAA ACAGCAATGG CGCGATTCCC  2211

CCGCCAACAC ATTCAAACAC CGCCTGATCC GCGCCTTGAC CAAAATCGGC AGGGAAAGGG  2271

AAAAACGCCG GCAAAGGCGC GAACAGTTAA TCGGCAAGAT TATTGTGCCT TTCCAATAAA  2331

AGGAGAAAAG ATG GAC ATC GTA TTT GCG GCA GAC GAC AAC TAT GCC GCC    2380
           Met Asp Ile Val Phe Ala Ala Asp Asp Asn Tyr Ala Ala
           1               5                   10

TAC CTT TGC GTT GCG GCA AAA AGC GTG GAA GCG GCC CAT CCC GAT ACG    2428
Tyr Leu Cys Val Ala Ala Lys Ser Val Glu Ala Ala His Pro Asp Thr
    15                  20                  25

GAA ATC AGG TTC CAC GTC CTC GAT GCC GGC ATC AGT GAG GAA AAC CGG    2476
Glu Ile Arg Phe His Val Leu Asp Ala Gly Ile Ser Glu Glu Asn Arg
30                  35                  40                  45

GCG GCG GTT GCC GCC AAT TTG CGG GGG GGG GGT AAT ATC CGC TTT ATA    2524
Ala Ala Val Ala Ala Asn Leu Arg Gly Gly Gly Asn Ile Arg Phe Ile
                50                  55                  60

GAC GTA AAC CCC GAA GAT TTC GCC GGC TTC CCC TTA AAC ATC AGG CAC    2572
Asp Val Asn Pro Glu Asp Phe Ala Gly Phe Pro Leu Asn Ile Arg His
            65                  70                  75

ATT TCC ATT ACG ACT TAT GCC CGC CTG AAA TTG GGC GAA TAC ATT GCC    2620
Ile Ser Ile Thr Thr Tyr Ala Arg Leu Lys Leu Gly Glu Tyr Ile Ala
        80                  85                  90

GAT TGC GAC AAA GTC CTG TAT CTG GAT ACG GAC GTA TTG GTC AGG GAC    2668
Asp Cys Asp Lys Val Leu Tyr Leu Asp Thr Asp Val Leu Val Arg Asp
    95                  100                 105

GGC CTG AAG CCC TTA TGG GAT ACC GAT TTG GGC GGT AAC TGG GTC GGC    2716
Gly Leu Lys Pro Leu Trp Asp Thr Asp Leu Gly Gly Asn Trp Val Gly
110                 115                 120                 125

GCG TGC ATC GAT TTG TTT GTC GAA AGG CAG GAA GGA TAC AAA CAA AAA    2764
Ala Cys Ile Asp Leu Phe Val Glu Arg Gln Glu Gly Tyr Lys Gln Lys
                130                 135                 140

ATC GGT ATG GCG GAC GGA GAA TAT TAT TTC AAT GCC GGC GTA TTG CTG    2812
Ile Gly Met Ala Asp Gly Glu Tyr Tyr Phe Asn Ala Gly Val Leu Leu
            145                 150                 155

ATC AAC CTG AAA AAG TGG CGG CGG CAC GAT ATT TTC AAA ATG TCC TGC    2860
Ile Asn Leu Lys Lys Trp Arg Arg His Asp Ile Phe Lys Met Ser Cys
```

```
                160                   165                      170
GAA TGG GTG GAA CAA TAC AAG GAC GTG ATG CAA TAT CAG GAT CAG GAC    2908
Glu Trp Val Glu Gln Tyr Lys Asp Val Met Gln Tyr Gln Asp Gln Asp
    175                 180                 185

ATT TTG AAC GGG CTG TTT AAA GGC GGG GTG TGT TAT GCG AAC AGC CGT    2956
Ile Leu Asn Gly Leu Phe Lys Gly Gly Val Cys Tyr Ala Asn Ser Arg
190                 195                 200                 205

TTC AAC TTT ATG CCG ACC AAT TAT GCC TTT ATG GCG AAC GGG TTT GCG    3004
Phe Asn Phe Met Pro Thr Asn Tyr Ala Phe Met Ala Asn Gly Phe Ala
                210                 215                 220

TCC CGC CAT ACC GAC CCG CTT TAC CTC GAC CGT ACC AAT ACG GCG ATG    3052
Ser Arg His Thr Asp Pro Leu Tyr Leu Asp Arg Thr Asn Thr Ala Met
            225                 230                 235

CCC GTC GCC GTC AGC CAT TAT TGC GGC TCG GCA AAG CCG TGG CAC AGG    3100
Pro Val Ala Val Ser His Tyr Cys Gly Ser Ala Lys Pro Trp His Arg
        240                 245                 250

GAC TGC ACC GTT TGG GGT GCG GAA CGT TTC ACA GAG TTG GCC GGC AGC    3148
Asp Cys Thr Val Trp Gly Ala Glu Arg Phe Thr Glu Leu Ala Gly Ser
    255                 260                 265

CTG ACG ACC GTT CCC GAA GAA TGG CGC GGC AAA CTT GCC GTC CCG CCG    3196
Leu Thr Thr Val Pro Glu Glu Trp Arg Gly Lys Leu Ala Val Pro Pro
270                 275                 280                 285

ACA AAG TGT ATG CTT CAA AGA TGG CGC AAA AAG CTG TCT GCC AGA TTC    3244
Thr Lys Cys Met Leu Gln Arg Trp Arg Lys Lys Leu Ser Ala Arg Phe
                290                 295                 300

TTA CGC AAG ATT TAT TGA CGGGGCAGGC CGTCTGAAGC CTTCAGACGG           3292
Leu Arg Lys Ile Tyr
                305

CATCGGACGT ATCGGAAAGG AGAAACGGA TTG CAG CCT TTA GTC AGC GTA TTG    3345
                               Leu Gln Pro Leu Val Ser Val Leu
                                 1               5

ATT TGC GCC TAC AAC GCA GAA AAA TAT TTT GCC CAA TCA TTG GCC GCC    3393
Ile Cys Ala Tyr Asn Ala Glu Lys Tyr Phe Ala Gln Ser Leu Ala Ala
    10                  15                  20

GTA GTG GGG CAG ACT TGG CGC AAC TTG GAT ATT TTG ATT GTC GAT GAC    3441
Val Val Gly Gln Thr Trp Arg Asn Leu Asp Ile Leu Ile Val Asp Asp
25                  30                  35                  40

GGC TCG ACG GAC GGC ACG CCC GCC ATT GCC CGG CAT TTC CAA GAA CAG    3489
Gly Ser Thr Asp Gly Thr Pro Ala Ile Ala Arg His Phe Gln Glu Gln
                45                  50                  55

GAC GGC AGG ATC AGG ATA ATT TCC AAT CCC CGC AAT TTG GGC TTT ATC    3537
Asp Gly Arg Ile Arg Ile Ile Ser Asn Pro Arg Asn Leu Gly Phe Ile
            60                  65                  70

GCC TCT TTA AAC ATC GGG CTG GAC GAA TTG GCA AAG TCG GGG GGG GGG    3585
Ala Ser Leu Asn Ile Gly Leu Asp Glu Leu Ala Lys Ser Gly Gly Gly
        75                  80                  85

GAA TAT ATT GCG CGC ACC GAT GCC GAC GAT ATT GCC TCC CCC GGC TGG    3633
Glu Tyr Ile Ala Arg Thr Asp Ala Asp Asp Ile Ala Ser Pro Gly Trp
    90                  95                  100

ATT GAG AAA ATC GTG GGC GAG ATG GAA AAA GAC CGC AGC ATC ATT GCG    3681
Ile Glu Lys Ile Val Gly Glu Met Glu Lys Asp Arg Ser Ile Ile Ala
105                 110                 115                 120

ATG GGC GCG TGG TTG GAA GTT TTG TCG GAA GAA AAC AAT AAA AGC GTG    3729
Met Gly Ala Trp Leu Glu Val Leu Ser Glu Glu Asn Asn Lys Ser Val
                125                 130                 135

CTT GCC GCC ATT GCC CGA AAC GGC GCA ATT TGG GAC AAA CCG ACC CGG    3777
Leu Ala Ala Ile Ala Arg Asn Gly Ala Ile Trp Asp Lys Pro Thr Arg
            140                 145                 150

CAT GAA GAC ATT GTC GCC GTT TTC CCT TTC GGC AAC CCC ATA CAC AAC    3825
```

-continued

```
         His Glu Asp Ile Val Ala Val Phe Pro Phe Gly Asn Pro Ile His Asn
             155                 160                 165

AAC ACG ATG ATT ATG AGG CGC AGC GTC ATT GAC GGC GGT TTG CGG TTC        3873
Asn Thr Met Ile Met Arg Arg Ser Val Ile Asp Gly Gly Leu Arg Phe
        170                 175                 180

GAT CCA GCC TAT ATC CAC GCC GAA GAC TAT AAG TTT TGG TAC GAA GCC        3921
Asp Pro Ala Tyr Ile His Ala Glu Asp Tyr Lys Phe Trp Tyr Glu Ala
185                 190                 195                 200

GGC AAA CTG GGC AGG CTG GCT TAT TAT CCC GAA GCC TTG GTC AAA TAC        3969
Gly Lys Leu Gly Arg Leu Ala Tyr Tyr Pro Glu Ala Leu Val Lys Tyr
                205                 210                 215

CGC TTC CAT CAA GAC CAG ACT TCT TCC AAA TAC AAC CTG CAA CAG CGC        4017
Arg Phe His Gln Asp Gln Thr Ser Ser Lys Tyr Asn Leu Gln Gln Arg
            220                 225                 230

AGG ACG GCG TGG AAA ATC AAA GAA GAA ATC AGG GCG GGG TAT TGG AAG        4065
Arg Thr Ala Trp Lys Ile Lys Glu Glu Ile Arg Ala Gly Tyr Trp Lys
        235                 240                 245

GCG GCA GGC ATA GCC GTC GGG GCG GAC TGC CTG AAT TAC GGG CTT TTG        4113
Ala Ala Gly Ile Ala Val Gly Ala Asp Cys Leu Asn Tyr Gly Leu Leu
    250                 255                 260

AAA TCA ACG GCA TAT GCG TTG TAC GAA AAA GCC TTG TCC GGA CAG GAT        4161
Lys Ser Thr Ala Tyr Ala Leu Tyr Glu Lys Ala Leu Ser Gly Gln Asp
265                 270                 275                 280

ATC GGA TGC CTC CGC CTG TTC CTG TAC GAA TAT TTC TTG TCG TTG GAA        4209
Ile Gly Cys Leu Arg Leu Phe Leu Tyr Glu Tyr Phe Leu Ser Leu Glu
                285                 290                 295

AAG TAT TCT TTG ACC GAT TTG CTG GAT TTC TTG ACA GAC CGC GTG ATG        4257
Lys Tyr Ser Leu Thr Asp Leu Leu Asp Phe Leu Thr Asp Arg Val Met
            300                 305                 310

AGG AAG CTG TTT GCC GCA CCG CAA TAT AGG AAA ATC CTG AAA AAA ATG        4305
Arg Lys Leu Phe Ala Ala Pro Gln Tyr Arg Lys Ile Leu Lys Lys Met
        315                 320                 325

TTA CGC CCT TGG AAA TAC CGC AGC TAT TGA AACCGAACAG GATAAATC ATG        4356
Leu Arg Pro Trp Lys Tyr Arg Ser Tyr                         Met
    330                 335                                   1

CAA AAC CAC GTT ATC AGC TTG GCT TCC GCC GCA GAG CGC AGG GCG CAC        4404
Gln Asn His Val Ile Ser Leu Ala Ser Ala Ala Glu Arg Arg Ala His
              5                  10                  15

ATT GCC GAT ACC TTC GGC AGT CGC GGC ATC CCG TTC CAG TTT TTC GAC        4452
Ile Ala Asp Thr Phe Gly Ser Arg Gly Ile Pro Phe Gln Phe Phe Asp
         20                  25                  30

GCA CTG ATG CCG TCT GAA AGG CTG GAA CAG GCG ATG GCG GAA CTC GTC        4500
Ala Leu Met Pro Ser Glu Arg Leu Glu Gln Ala Met Ala Glu Leu Val
     35                  40                  45

CCC GGC TTG TCG GCG CAC CCC TAT TTG AGC GGA GTG GAA AAA GCC TGC        4548
Pro Gly Leu Ser Ala His Pro Tyr Leu Ser Gly Val Glu Lys Ala Cys
 50                  55                  60                  65

TTT ATG AGC CAC GCC GTA TTG TGG GAA CAG GCG TTG GAT GAA GGT CTG        4596
Phe Met Ser His Ala Val Leu Trp Glu Gln Ala Leu Asp Glu Gly Leu
             70                  75                  80

CCG TAT ATC GCC GTA TTT GAG GAC GAC GTT TTA CTC GGC GAA GGC GCG        4644
Pro Tyr Ile Ala Val Phe Glu Asp Asp Val Leu Leu Gly Glu Gly Ala
         85                  90                  95

GAG CAG TTC CTT GCC GAA GAT ACT TGG TTG GAA GAG CGT TTT GAC AAG        4692
Glu Gln Phe Leu Ala Glu Asp Thr Trp Leu Glu Glu Arg Phe Asp Lys
    100                 105                 110

GAT TCC GCC TTT ATC GTC CGT TTG GAA ACG ATG TTT GCG AAA GTT ATT        4740
Asp Ser Ala Phe Ile Val Arg Leu Glu Thr Met Phe Ala Lys Val Ile
115                 120                 125
```

```
GTC AGA CCG GAT AAA GTC CTG AAT TAT GAA AAC CGG TCA TTT CCT TTG         4788
Val Arg Pro Asp Lys Val Leu Asn Tyr Glu Asn Arg Ser Phe Pro Leu
130                 135                 140                 145

CTG GAG AGC GAA CAT TGT GGG ACG GCT GGC TAT ATC ATT TCG CGT GAG         4836
Leu Glu Ser Glu His Cys Gly Thr Ala Gly Tyr Ile Ile Ser Arg Glu
                150                 155                 160

GCG ATG CGG TTT TTC TTG GAC AGG TTT GCC GTT TTG CCG CCA GAG CGG         4884
Ala Met Arg Phe Phe Leu Asp Arg Phe Ala Val Leu Pro Pro Glu Arg
            165                 170                 175

ATT AAA GCG GTA GAT TTG ATG ATG TTT ACT TAT TTC TTT GAT AAG GAG         4932
Ile Lys Ala Val Asp Leu Met Met Phe Thr Tyr Phe Phe Asp Lys Glu
        180                 185                 190

GGG ATG CCT GTT TAT CAG GTT AGT CCC GCC TTA TGT ACC CAA GAA TTG         4980
Gly Met Pro Val Tyr Gln Val Ser Pro Ala Leu Cys Thr Gln Glu Leu
    195                 200                 205

CAT TAT GCC AAG TTT CTC AGT CAA AAC AGT ATG TTG GGT AGC GAT TTG         5028
His Tyr Ala Lys Phe Leu Ser Gln Asn Ser Met Leu Gly Ser Asp Leu
210                 215                 220                 225

GAA AAA GAT AGG GAA CAA GGA AGA AGA CAC CGC CGT TCG TTG AAG GTG         5076
Glu Lys Asp Arg Glu Gln Gly Arg Arg His Arg Arg Ser Leu Lys Val
                230                 235                 240

ATG TTT GAC TTG AAG CGT GCT TTG GGT AAA TTC GGT AGG GAA AAG AAG         5124
Met Phe Asp Leu Lys Arg Ala Leu Gly Lys Phe Gly Arg Glu Lys Lys
            245                 250                 255

AAA AGA ATG GAG CGT CAA AGG CAG GCG GAG CTT GAG AAA GTT TAC GGC         5172
Lys Arg Met Glu Arg Gln Arg Gln Ala Glu Leu Glu Lys Val Tyr Gly
        260                 265                 270

AGG CGG GTC ATA TTG TTC AAA TAG TTTGTGTAAA ATATAGGGGA TTAAAATCAG        5226
Arg Arg Val Ile Leu Phe Lys
    275                 280

AAATGGACAC ACTGTCATTC CCGCGCAGGC GGGAATCTAG GTCTTTAAAC TTCGGTTTTT       5286

TCCGATAAAT TCTTGCCGCA TTAAAATTCC AGATTCCCGC TTTCGCGGGG ATGACGGCGG       5346

GGGGATTGTT GCTTTTTCGG ATAAAATCCC GTGTTTTTTC ATCTGCTAGG TAAAATCGCC       5406

CCAAAGCGTC TGCATCGCGG CGATGGCGGC GAGTGGGGCG GTTTCTGTGC GTAAAATCCG       5466

TTTTCCGAGT GTAACCGCCT GAAAGCCGGC TTCAAATGCC TGTTGTTCTT CCTGTTCTGT       5526

CCAGCCGCCT TCGGGCCCGA CCATAAAGAC GATTGCGCCG GACGGGTGGC GGATGTCGCC       5586

GAGTTTGCAG GCGCGGTTGA TGCTCATAAT CAGCTTGGTG TTTTCAGACG GCATTTTGTC       5646

GAGTGCTTCA CGGTAGCCGA TGATGGGCAG TACGGGGGA ACGGTGTTCC TGCCGCTTTG        5706

TTCGCACGCG GAGATGACGA TTTCCTGCCA GCGTGCGAGG CGTTTGGCGG CGCGTTCTCC       5766

GTCGAGGCGG ACGATGCAGC GTTCGCTGAT GACGGGCTGT ATGGCGGTTA CGCCGAGTTC       5826

GACGCTTTTT TGCAGGGTGA AATCCATGCG ATC                                    5859

(2) INFORMATION FOR SEQ ID NO:2:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:2:

Leu Gln Ala Val Ala Val Phe Lys Gln Leu Pro Glu Ala Ala Ala Leu
 1               5                  10                  15

Ala Ala Ala Asn Lys Arg Val Gln Asn Leu Leu Lys Lys Ala Asp Ala
            20                  25                  30
```

```
Ala Leu Gly Glu Val Asn Glu Ser Leu Leu Gln Gln Asp Glu Glu Lys
            35                  40                  45

Ala Leu Tyr Ala Ala Ala Gln Gly Leu Gln Pro Lys Ile Ala Ala Ala
        50                  55                  60

Val Ala Glu Gly Asn Phe Arg Thr Ala Leu Ser Glu Leu Ala Ser Val
 65                  70                  75                  80

Lys Pro Gln Val Asp Ala Phe Phe Asp Gly Val Met Val Met Ala Glu
                85                  90                  95

Asp Ala Ala Val Lys Gln Asn Arg Leu Asn Leu Leu Asn Arg Leu Ala
               100                 105                 110

Glu Gln Met Asn Ala Val Ala Asp Ile Ala Leu Leu Gly Glu
        115                 120                 125
```

(2) INFORMATION FOR SEQ ID NO:3:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:3:

```
Leu Gln Pro Leu Val Ser Val Leu Ile Cys Ala Tyr Asn Val Glu Lys
 1                   5                  10                  15

Tyr Phe Ala Gln Ser Leu Ala Ala Val Val Asn Gln Thr Trp Arg Asn
                20                  25                  30

Leu Asp Ile Leu Ile Val Asp Asp Gly Ser Thr Asp Gly Thr Leu Ala
            35                  40                  45

Ile Ala Lys Asp Phe Gln Lys Arg Asp Ser Arg Ile Lys Ile Leu Ala
        50                  55                  60

Gln Ala Gln Asn Ser Gly Leu Ile Pro Ser Leu Asn Ile Gly Leu Asp
 65                  70                  75                  80

Glu Leu Ala Lys Ser Gly Gly Gly Gly Glu Tyr Ile Ala Arg Thr
                85                  90                  95

Asp Ala Asp Asp Ile Ala Ser Pro Gly Trp Ile Glu Lys Ile Val Gly
               100                 105                 110

Glu Met Glu Lys Asp Arg Ser Ile Ile Ala Met Gly Ala Trp Leu Glu
        115                 120                 125

Val Leu Ser Glu Glu Lys Asp Gly Asn Arg Leu Ala Arg His His Lys
130                 135                 140

His Gly Lys Ile Trp Lys Lys Pro Thr Arg His Glu Asp Ile Ala Ala
145                 150                 155                 160

Phe Phe Pro Phe Gly Asn Pro Ile His Asn Asn Thr Met Ile Met Arg
                165                 170                 175

Arg Ser Val Ile Asp Gly Gly Leu Arg Tyr Asp Thr Glu Arg Asp Trp
            180                 185                 190

Ala Glu Asp Tyr Gln Phe Trp Tyr Asp Val Ser Lys Leu Gly Arg Leu
        195                 200                 205

Ala Tyr Tyr Pro Glu Ala Leu Val Lys Tyr Arg Leu His Ala Asn Gln
        210                 215                 220

Val Ser Ser Lys His Ser Val Arg Gln His Glu Ile Ala Gln Gly Ile
225                 230                 235                 240

Gln Lys Thr Ala Arg Asn Asp Phe Leu Gln Ser Met Gly Phe Lys Thr
                245                 250                 255
```

```
Arg Phe Asp Ser Leu Glu Tyr Arg Gln Thr Lys Ala Ala Tyr Glu
            260                 265                 270

Leu Pro Glu Lys Asp Leu Pro Glu Glu Asp Phe Glu Arg Ala Arg Arg
            275                 280                 285

Phe Leu Tyr Gln Cys Phe Lys Arg Thr Asp Thr Pro Pro Ser Gly Ala
            290                 295                 300

Trp Leu Asp Phe Ala Ala Asp Gly Arg Met Arg Arg Leu Phe Thr Leu
305                 310                 315                 320

Arg Gln Tyr Phe Gly Ile Leu Tyr Arg Leu Ile Lys Asn Arg Arg Gln
                325                 330                 335

Ala Arg Ser Asp Ser Ala Gly Lys Glu Gln Glu Ile
            340                 345

(2) INFORMATION FOR SEQ ID NO:4:

(i) SEQUENCE CHARACTERISTICS:
        (A) LENGTH: 306 amino acids
        (B) TYPE: amino acid
        (D) TOPOLOGY: linear (ii) MOLECULE TYPE: protein (xi) SEQUENCE DESCRIPTION: SEQ ID NO:4:

Met Asp Ile Val Phe Ala Ala Asp Asp Asn Tyr Ala Ala Tyr Leu Cys
  1               5                  10                  15

Val Ala Ala Lys Ser Val Glu Ala Ala His Pro Asp Thr Glu Ile Arg
             20                  25                  30

Phe His Val Leu Asp Ala Gly Ile Ser Glu Glu Asn Arg Ala Ala Val
             35                  40                  45

Ala Ala Asn Leu Arg Gly Gly Asn Ile Arg Phe Ile Asp Val Asn
 50                  55                  60

Pro Glu Asp Phe Ala Gly Phe Pro Leu Asn Ile Arg His Ile Ser Ile
 65                  70                  75                  80

Thr Thr Tyr Ala Arg Leu Lys Leu Gly Glu Tyr Ile Ala Asp Cys Asp
             85                  90                  95

Lys Val Leu Tyr Leu Asp Thr Asp Val Leu Val Arg Asp Gly Leu Lys
            100                 105                 110

Pro Leu Trp Asp Thr Asp Leu Gly Gly Asn Trp Val Gly Ala Cys Ile
            115                 120                 125

Asp Leu Phe Val Glu Arg Gln Glu Gly Tyr Lys Gln Lys Ile Gly Met
130                 135                 140

Ala Asp Gly Glu Tyr Tyr Phe Asn Ala Gly Val Leu Leu Ile Asn Leu
145                 150                 155                 160

Lys Lys Trp Arg Arg His Asp Ile Phe Lys Met Ser Cys Glu Trp Val
                165                 170                 175

Glu Gln Tyr Lys Asp Val Met Gln Tyr Gln Asp Gln Asp Ile Leu Asn
            180                 185                 190

Gly Leu Phe Lys Gly Gly Val Cys Tyr Ala Asn Ser Arg Phe Asn Phe
            195                 200                 205

Met Pro Thr Asn Tyr Ala Phe Met Ala Asn Gly Phe Ala Ser Arg His
            210                 215                 220

Thr Asp Pro Leu Tyr Leu Asp Arg Thr Asn Thr Ala Met Pro Val Ala
225                 230                 235                 240

Val Ser His Tyr Cys Gly Ser Ala Lys Pro Trp His Arg Asp Cys Thr
                245                 250                 255

Val Trp Gly Ala Glu Arg Phe Thr Glu Leu Ala Gly Ser Leu Thr Thr
```

```
                    260                 265                 270
Val Pro Glu Glu Trp Arg Gly Lys Leu Ala Val Pro Pro Thr Lys Cys
                275                 280                 285

Met Leu Gln Arg Trp Arg Lys Lys Leu Ser Ala Arg Phe Leu Arg Lys
    290                 295                 300

Ile Tyr
305

(2) INFORMATION FOR SEQ ID NO:5:

(i) SEQUENCE CHARACTERISTICS:
        (A) LENGTH: 337 amino acids
        (B) TYPE: amino acid
        (D) TOPOLOGY: linear (ii) MOLECULE TYPE: protein (xi) SEQUENCE DESCRIPTION: SEQ ID NO:5:

Leu Gln Pro Leu Val Ser Val Leu Ile Cys Ala Tyr Asn Ala Glu Lys
  1                   5                  10                  15

Tyr Phe Ala Gln Ser Leu Ala Ala Val Val Gly Gln Thr Trp Arg Asn
                 20                  25                  30

Leu Asp Ile Leu Ile Val Asp Asp Gly Ser Thr Asp Gly Thr Pro Ala
             35                  40                  45

Ile Ala Arg His Phe Gln Glu Gln Asp Gly Arg Ile Arg Ile Ile Ser
         50                  55                  60

Asn Pro Arg Asn Leu Gly Phe Ile Ala Ser Leu Asn Ile Gly Leu Asp
 65                  70                  75                  80

Glu Leu Ala Lys Ser Gly Gly Glu Tyr Ile Ala Arg Thr Asp Ala
                 85                  90                  95

Asp Asp Ile Ala Ser Pro Gly Trp Ile Glu Lys Ile Val Gly Glu Met
            100                 105                 110

Glu Lys Asp Arg Ser Ile Ile Ala Met Gly Ala Trp Leu Glu Val Leu
        115                 120                 125

Ser Glu Glu Asn Asn Lys Ser Val Leu Ala Ala Ile Ala Arg Asn Gly
    130                 135                 140

Ala Ile Trp Asp Lys Pro Thr Arg His Glu Asp Ile Val Ala Val Phe
145                 150                 155                 160

Pro Phe Gly Asn Pro Ile His Asn Asn Thr Met Ile Met Arg Arg Ser
                165                 170                 175

Val Ile Asp Gly Gly Leu Arg Phe Asp Pro Ala Tyr Ile His Ala Glu
            180                 185                 190

Asp Tyr Lys Phe Trp Tyr Glu Ala Gly Lys Leu Gly Arg Leu Ala Tyr
        195                 200                 205

Tyr Pro Glu Ala Leu Val Lys Tyr Arg Phe His Gln Asp Gln Thr Ser
    210                 215                 220

Ser Lys Tyr Asn Leu Gln Gln Arg Arg Thr Ala Trp Lys Ile Lys Glu
225                 230                 235                 240

Glu Ile Arg Ala Gly Tyr Trp Lys Ala Ala Gly Ile Ala Val Gly Ala
                245                 250                 255

Asp Cys Leu Asn Tyr Gly Leu Leu Lys Ser Thr Ala Tyr Ala Leu Tyr
            260                 265                 270

Glu Lys Ala Leu Ser Gly Gln Asp Ile Gly Cys Leu Arg Leu Phe Leu
        275                 280                 285

Tyr Glu Tyr Phe Leu Ser Leu Glu Lys Tyr Ser Leu Thr Asp Leu Leu
    290                 295                 300
```

```
Asp Phe Leu Thr Asp Arg Val Met Arg Lys Leu Phe Ala Ala Pro Gln
305                 310                 315                 320

Tyr Arg Lys Ile Leu Lys Lys Met Leu Arg Pro Trp Lys Tyr Arg Ser
            325                 330                 335

Tyr
```

(2) INFORMATION FOR SEQ ID NO:6:

(i) SEQUENCE CHARACTERISTICS:
        (A) LENGTH: 280 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gln Asn His Val Ile Ser Leu Ala Ser Ala Ala Glu Arg Arg Ala
 1               5                  10                  15

His Ile Ala Asp Thr Phe Gly Ser Arg Gly Ile Pro Phe Gln Phe Phe
                20                  25                  30

Asp Ala Leu Met Pro Ser Glu Arg Leu Glu Gln Ala Met Ala Glu Leu
            35                  40                  45

Val Pro Gly Leu Ser Ala His Pro Tyr Leu Ser Gly Val Glu Lys Ala
 50                  55                  60

Cys Phe Met Ser His Ala Val Leu Trp Glu Gln Ala Leu Asp Glu Gly
 65                  70                  75                  80

Leu Pro Tyr Ile Ala Val Phe Glu Asp Val Leu Leu Gly Glu Gly
                85                  90                  95

Ala Glu Gln Phe Leu Ala Glu Asp Thr Trp Leu Glu Glu Arg Phe Asp
                100                 105                 110

Lys Asp Ser Ala Phe Ile Val Arg Leu Glu Thr Met Phe Ala Lys Val
            115                 120                 125

Ile Val Arg Pro Asp Lys Val Leu Asn Tyr Glu Asn Arg Ser Phe Pro
130                 135                 140

Leu Leu Glu Ser Glu His Cys Gly Thr Ala Gly Tyr Ile Ile Ser Arg
145                 150                 155                 160

Glu Ala Met Arg Phe Phe Leu Asp Arg Phe Ala Val Leu Pro Pro Glu
                165                 170                 175

Arg Ile Lys Ala Val Asp Leu Met Met Phe Thr Tyr Phe Phe Asp Lys
            180                 185                 190

Glu Gly Met Pro Val Tyr Gln Val Ser Pro Ala Leu Cys Thr Gln Glu
        195                 200                 205

Leu His Tyr Ala Lys Phe Leu Ser Gln Asn Ser Met Leu Gly Ser Asp
210                 215                 220

Leu Glu Lys Asp Arg Glu Gln Gly Arg Arg His Arg Arg Ser Leu Lys
225                 230                 235                 240

Val Met Phe Asp Leu Lys Arg Ala Leu Gly Lys Phe Gly Arg Glu Lys
                245                 250                 255

Lys Lys Arg Met Glu Arg Gln Arg Gln Ala Glu Leu Glu Lys Val Tyr
            260                 265                 270

Gly Arg Arg Val Ile Leu Phe Lys
            275                 280
```

(2) INFORMATION FOR SEQ ID NO:7:

(i) SEQUENCE CHARACTERISTICS:

(A) LENGTH: 6 amino acids
        (B) TYPE: amino acid
        (C) STRANDEDNESS: double
        (D) TOPOLOGY: linear (ii) MOLECULE TYPE: protein (xi) SEQUENCE DESCRIPTION: SEQ ID NO:7:

Tyr Ser Arg Asp Ser Ser
 1               5

(2) INFORMATION FOR SEQ ID NO:8:

(i) SEQUENCE CHARACTERISTICS:
        (A) LENGTH: 348 amino acids
        (B) TYPE: amino acid
        (C) STRANDEDNESS: double
        (D) TOPOLOGY: linear (ii) MOLECULE TYPE: protein (iv) ANTI-SENSE: NO (xi) SEQUENCE DESCRIPTION: SEQ ID NO:8:

Leu Gln Pro Leu Val Ser Val Leu Ile Cys Ala Tyr Asn Val Glu Lys
 1               5                  10                  15

Tyr Phe Ala Gln Ser Leu Ala Ala Val Val Asn Gln Thr Trp Arg Asn
                20                  25                  30

Leu Asp Ile Leu Ile Val Asp Asp Gly Ser Thr Asp Gly Thr Leu Ala
            35                  40                  45

Ile Ala Lys Asp Phe Gln Lys Arg Asp Ser Arg Ile Lys Ile Leu Ala
        50                  55                  60

Gln Ala Gln Asn Ser Gly Leu Ile Pro Ser Leu Asn Ile Gly Leu Asp
65                  70                  75                  80

Glu Leu Ala Lys Ser Gly Gly Gly Gly Glu Tyr Ile Ala Arg Thr
                85                  90                  95

Asp Ala Asp Asp Ile Ala Ser Pro Gly Trp Ile Glu Lys Ile Val Gly
                100                 105                 110

Glu Met Glu Lys Asp Arg Ser Ile Ile Ala Met Gly Ala Trp Leu Glu
            115                 120                 125

Val Leu Ser Glu Glu Lys Asp Gly Asn Arg Leu Ala Arg His His Lys
        130                 135                 140

His Gly Lys Ile Trp Lys Lys Pro Thr Arg His Glu Asp Ile Ala Ala
145                 150                 155                 160

Phe Phe Pro Phe Gly Asn Pro Ile His Asn Asn Thr Met Ile Met Arg
                165                 170                 175

Arg Ser Val Ile Asp Gly Gly Leu Arg Tyr Asp Thr Glu Arg Asp Trp
            180                 185                 190

Ala Glu Asp Tyr Gln Phe Trp Tyr Asp Val Ser Lys Leu Gly Arg Leu
        195                 200                 205

Ala Tyr Tyr Pro Glu Ala Leu Val Lys Tyr Arg Leu His Ala Asn Gln
        210                 215                 220

Val Ser Ser Lys His Ser Val Arg Gln His Glu Ile Ala Gln Gly Ile
225                 230                 235                 240

Gln Lys Thr Ala Arg Asn Asp Phe Leu Gln Ser Met Gly Phe Lys Thr
                245                 250                 255

Arg Phe Asp Ser Leu Glu Tyr Arg Gln Thr Lys Ala Ala Ala Tyr Glu
            260                 265                 270

Leu Pro Glu Lys Asp Leu Pro Glu Glu Asp Phe Glu Arg Ala Arg Arg

-continued

```
              275                 280                 285
Phe Leu Tyr Gln Cys Phe Lys Arg Thr Asp Thr Pro Pro Ser Gly Ala
        290                 295                 300

Trp Leu Asp Phe Ala Ala Asp Gly Arg Met Arg Arg Leu Phe Thr Leu
305                 310                 315                 320

Arg Gln Tyr Phe Gly Ile Leu Tyr Arg Leu Ile Lys Asn Arg Arg Gln
                325                 330                 335

Ala Arg Ser Asp Ser Ala Gly Lys Glu Gln Glu Ile
                340                 345
```

METHOD OF TRANSFERRING AT LEAST TWO SACCHARIDE UNITS WITH A POLYGLYCOSYLTRANSFERASE

This application is a continuation application of application Ser. No. 08/478,140 filed Jun. 7, 1995 now U.S. Pat. No. 6,127,153, which is incorporated by reference herein in its entirety.

BACKGROUND OF THE INVENTION

1. Field of the Invention

The present invention relates to a method of transferring at least two saccharide units with a polyglycosyltransferase, a polyglycosyltransferase and a gene encoding such a polyglycosyltransferase.

2. Discussion of the Background

Biosynthesis of Oligosaccharides

Oligosaccharides are polymers of varying number of residues, linkages, and subunits. The basic subunit is a carbohydrate monosaccharide or sugar, such as mannose, glucose, galactose, N-acetylglucosamine, N-acetylgalactosamine, and the like. The number of different possible stereoisomeric oligosaccharide chains is enormous.

Oligosaccharides and polysaccharides play an important role in protein function and activity, by serving as half-life modulators, and, in some instances, by providing structure. Oligosaccharides are critical to the antigenic variability, and hence immune evasion, of Neisseria, especially gonococcus.

Numerous classical techniques for the synthesis of carbohydrates have been developed, but these techniques suffer the difficulty of requiring selective protection and deprotection. Organic synthesis of oligosaccharides is further hampered by the lability of many glycosidic bonds, difficulties in achieving regioselective sugar coupling, and generally low synthetic yields. In short, unlike the experience with peptide synthesis, traditional synthetic organic chemistry cannot provide for quantitative, reliable synthesis of even fairly simple oligosaccharides.

Recent advances in oligosaccharide synthesis have occurred with the isolation of glycosyltransferases from natural sources. These enzymes can be used in vitro to prepare oligosaccharides and polysaccharides (see, e.g., Roth, U.S. Pat. No. 5,180,674). The advantage of biosynthesis with glycosyltransferases is that the glycosidic linkages formed by enzymes are highly stereo and regiospecific. However, each enzyme catalyzes linkage of specific sugar donor residues to other specific acceptor molecules, e.g., an oligosaccharide or lipid. Thus, synthesis of a desired oligosaccharide has required the use of a different glycosyltransferase for each different saccharide unit being transferred.

More specifically, such glycosyltransferases have only provided for the transfer of a single saccharide unit, specific for the glycosyltransferase. For example, a galactosyltransferase would transfer only galactose, a glucosyltransferase would transfer only glucose, an N-acetylglucosaminlytransferase would transfer only N-acetylglucosamine and a sialyl transferase would transfer only sialic acid.

However, the lack of generality of glycosyltransferases makes it necessary to use a different glycosyltransferase for every different sugar donor being transferred. As the usefulness of oligosaccharide compounds expands, the ability to transfer more than one sugar donor would provide a tremendous advantage, by decreasing the number of glycosyltransferases necessary to form necessary glycosidic bonds.

In addition, a glycosyltransferase which transferred at least two different sugar donors would be advantageous in synthesizing two glycosidic bonds of at least a trisaccharide, using the same glycosyltransferase.

A locus involved in the biosynthesis of gonococcal lipooligosaccharide (LOS) has been reported as being cloned from the gonococcal strain F62 (Gotschlich J. Exp. Med. (1994) 180, 2181–2190). Five genes lgtA, lgtB, lgtC, lgtD and lgtE are reported, and based on deletion experiments, activities are postulated, as encoding for glycosyltransferases. Due to the uncertainty caused by the nature of the deletion experiments, the exact activity of the proteins encoded by each of the genes was not ascertained and some of the genes are only suggested as being responsible for one or another activity, in the alternative. The gene lgtA is suggested as most likely to code for a GlcNAc transferase.

The transfer of more than one different saccharide moiety, by a polyglycosyltransferase has heretofore been unreported.

SUMMARY OF THE INVENTION

The present invention is directed to a method of transferring at least two saccharide units with a polyglycosyltransferase, a polyglycosyltransferase and nucleic acids encoding a polyglycosyltransferase.

Accordingly, in one aspect, the invention is directed to a method of transferring at least two saccharide units with a polyglycosyltransferase.

Accordingly, another aspect of the invention is directed to a method of transferring at least two saccharide units with a polyglycosyltransferase, which transfers both GlcNAc, and GalNAc, from the corresponding sugar nucleotides to a sugar acceptor.

According to another aspect of the invention, a polyglycosyltransferase is obtained from a bacteria of the genus Neisseria, Escherichia or Pseudomonas.

Another aspect of the invention, is directed to a method of making at least two oligosaccharide compounds, from the same acceptor, with a polyglycosyltransferase.

Another aspect of the invention is directed to a method of making at least two oligosaccharide compounds from the same acceptor with a polyglycosyltransferase, which transfers both GlcNAc and GalNAc from the corresponding sugar nucleotides to the sugar acceptor.

Another embodiment of the present invention is directed to a method of transferring an N-acetylgalactosamine using a glycosyltransferase of SEQ ID NO: 8.

In specific embodiments, the invention relates to a nucleic acid that has a nucleotide sequence which encodes for the polypeptide sequence shown in SEQ ID NO. 8.

The functionally active polyglycosyltransferase of the invention is characterized by catalyzing both the addition of GalNAc β1→3 to Gal and the addition of GlcNAc β1→3 to Gal.

BRIEF DESCRIPTION OF THE DRAWINGS

FIGS. 1A–1B: provides the amino acid sequence of a polyglycosyltransferase of SEQ ID NO: 8.

FIGS. 2A–2H: provides the polynucleotide sequence of a LOS encoding gene isolated from *N. gonorrhoeae*(SEQ ID NO:1), of which nucleotides 445–1488 encode for a polyglycosyltransferase.

DETAILED DESCRIPTION OF THE INVENTION

As disclosed above, the present invention provides for a method of transferring at least two saccharide units with a polyglycosyltransferase, a gene encoding for a polyglycosyltransferase, and a polyglycosyltransferase. The polyglycosyltransferases of the invention can be used for in vitro biosynthesis of various oligosaccharides, such as the core oligosaccharide of the human blood group antigens, i.e., lacto-N-neotetraose.

Cloning and expression of a polyglycosyltransferase of the invention can be accomplished using standard techniques, as disclosed herein. Such a polyglycosyltransferase is useful for biosynthesis of oligosaccharides in vitro, or alternatively genes encoding such a polyglycosyltransferase can be transfected into cells, e.g., yeast cells or eukaryotic cells, to provide for alternative glycosylation of proteins and lipids.

The instant invention is based, in part, on the discovery that a polyglycosyltransferase isolated from Neisseria gonorrhoeae is capable of transferring both GlcNAc β1-3 to Gal and GalNAc β1-3 to Gal, from the corresponding sugar nucleotides.

An operon encoding five proteins having glycosyltransferase activity, is reported by Gotschlich, U.S. Pat. No. 5,545,553, by cloning of a locus involved in the biosynthesis of gonococcal LOS, strain F62. The protein sequence identified as SEQ ID NO: 8, a 348 amino acid protein, has now been discovered to have a polyglycosyltransferase activity. More specifically, the protein sequence identified herein as SEQ ID NO: 8 has been discovered to transfer both GlcNAc β1-3 to Gal and GalNAc β1-3 to Gal, from the corresponding sugar nucleotides.

In addition to the protein sequence SEQ ID NO: 8 the nucleotide sequence encoding this protein sequence reported in U.S. Pat. No. 5,545,553, a new polyglycosyltransferase has been discovered which transfers two different sugar units. This protein is similar to the protein of SEQ ID: 8, with the deletion of one or two of the five glycine units occurring between amino acid nos 86–90 of lgtA. In addition, it has been determined that an additional amino acid sequence -Tyr-Ser-Arg-Asp-Ser-Ser (SEQ ID NO:7), can be appended to the carboxy terminus of Ile (amino acid no 348) of SEQ ID NO: 3, while retaining the polyglycosyltransferase activity.

A polynucleotide sequence encoding for a polyglycosyltransferase is similar to the sequence of nucleotides 445 to 1488 of an LOS isolated from N. gonorrhoeae (see FIG. 2 (SEQ ID NO:1)) in which three or six of the guanine units occuring between nucleotides 700 to 715 have been deleted.

Another polynucleotide sequence is similar to the sequence of nucleotides 445 to 1488 of an LOS isolated from N. gonorrhoeae (see FIG. 2), in which nucleic acids sufficient to encode the amino acid sequence -Tyr-Ser-Arg-Asp-Ser-Ser (SEQ ID NO:7), can be appended to nucleotide 1488 and the protein encoded by the nucleotide sequence (i.e., nucleotides 445 to 1488 plus the appended sequence) retains polyglycosyltransferase activity.

Abbreviations used throughout this specification include: Lipopolysaccharide, LPS; Lipooligosaccharide, LOS; N-Acetyl-neuraminic acid cytidine mono phosphate, CMP-NANA; wild type, wt; Gal, galactose; Glc, glucose; NAc, N-acetyl (e.g., GalNAc or GlcNAc).

Isolation of Genes for Polyglycosyltransferases

Any Neisseria bacterial cell can potentially serve as the nucleic acid source for the molecular cloning of a polyglycosyltransferase gene. In a specific embodiment, infra, the genes are isolated from Neisseria gonorrhoeae. The DNA may be obtained by standard procedures known in the art from cloned DNA (e.g., a DNA "library'), by chemical synthesis, by CDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. 1, II). For example, a N. gonorrhoeae genomic DNA can be digested with a restriction endonuclease or endonucleases, e.g., Sau3A, into a phage vector digested with a restriction endonuclease or endonucleases, e.g., BamHI/EcoRI, for creation of a phage genomic library. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired polyglycosyltransferase gene may be accomplished in a number of ways. For example, the generated DNA fragments may be screened by nucleic acid hybridization to the labeled probe synthesized with a sequence as disclosed herein (Benton and Davis, 1977, Science 196:180; Grunstein and Hogness, 1975, Proc. Natl. Acad. Sci. U.S.A. 72:3961). Those DNA fragments with substantial homology to the probe will hybridize.

Suitable probes can be generated by PCR using random primers. In particular a probe which will hybridize to the polynucleotide sequence encoding for a four or five glycine residue (i.e., a twelve or fifteen guanine residue) would be a suitable probe for a polyglycosyltransferase.

The presence of a gene encoding a polyglycotransferase may be detected by assays based on the physicals chemical, or immunological properties of its expressed product. For example, these assays may screen for DNA clones that produce a protein that, e.g., has similar or identical electrophoretic migration, isoelectric focusing behavior, proteolytic digestion maps, or functional properties, in particular polyglycosyltransferase activity, the ability of a polyglycosyltransferase protein to mediate transfer of two different saccharide units to an acceptor molecule.

Alternatives to isolating a polyglycosyltransferase genomic DNA include, but are not limited to, chemically synthesizing the gene sequence itself from a known sequence that encodes a polyglycosyltransferase. In another embodiment, DNA for a polyglycosyltransferase gene can be isolated by PCR using oligonucleotide primers designed from the nucleotide sequences disclosed herein. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. In a specific aspect of the invention, the polyglycosyltransferase coding sequence is inserted in an E. coli cloning vector. Other examples of vectors include, but are not limited to, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In a specific embodiment, PCR primers containing such linker sites can be used to amplify the DNA for cloning. Recombinant molecules can be introduced into host cells via transformation, transfection, infection, electroporation, etc., so that many copies of the gene sequence are generated.

Transformation of host cells with recombinant DNA molecules that incorporate the isolated polyglycosyltransferase gene or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The present invention also relates to vectors containing genes encoding truncated forms of the enzyme (fragments) and derivatives of polyglycosyltransferases that have the same functional activity as a polyglycosvltransferase. The production and use of fragments and derivatives related to polyglycosyltransferases are within the scope of the present invention. In a specific embodiment, the fragment or derivative is functionally active, i.e., capable of mediating transfer of two different sugar donors to acceptor moieties.

Truncated fragments of the polyglycosyltransferases can be prepared by eliminating N-terminal, C-terminal, or internal regions of the protein that are not required for functional activity. Usually, such portions that are eliminated will include only a few, e.g., between 1 and 5, amino acid residues, but larger segments may be removed.

Chimeric molecules, e.g., fusion proteins, containing all or a functionally active portion of a polyglycosyltransferase of the invention joined to another protein are also envisioned. A polyglycosyltransferase fusion protein comprises at least a functionally active portion of a non-glycosyltransferase protein joined via a peptide bond to at least a functionally active portion of a polyglycosyltransferase polypeptide. The non-glycosyltransferase sequences can be amino- or carboxy-terminal to the polyglycosyltransferase sequences. Expression of a fusion protein can result in an enzymatically inactive polyglycosyltransferase fusion protein. A recombinant DNA molecule encoding such a fusion protein comprises a sequence encoding at least a functionally active portion of a non-glycosyltransferase protein joined in-frame to the polyglycosyltransferase coding sequence, and preferably encodes a cleavage site for a specific protease, e.g., thrombin or Factor Xa, preferably at the polyglycosyltransferase-non-glycosyltransferase juncture. In a specific embodiment, the fusion protein may be expressed in *Escherichia coli*.

If In particular, polyglycosyltransferase derivatives can be made by altering encoding nucleic acid sequences by substitutions, additions or deletions that provide for functionally equivalent molecules. Due to the degeneracy of nucleotide coding sequences, other DNA sequences which encode substantially the same amino acid sequence as a polyglycosyltransferase gene may be used in the practice of the present invention. These include but are not limited to nucleotide sequences comprising all or portions of polyglycosyltransferase genes that are altered by the substitution of different codons that encode the same amino acid residue within the sequence, thus producing a silent change. Likewise, the polyglycosyltransferase derivatives of the invention include, but are not limited to, those containing, as a primary amino acid sequence, all or part of the amino acid sequence of a polyglycosyltransferase including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding polyglycosyltransferase derivatives and analogs of the invention can be produced by various methods known in the art (e.g., Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of polyglycosyltransferase, care should be taken to ensure that the modified gene remains within the same translational reading frame as the polyglycosyltransferase gene, uninterrupted by translational stop signals, in the gene region where the desired activity is encoded.

Additionally, the polyglycosyltransferase nucleic acid sequence can be mutated in vitro or in viva, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TABO linkers (Pharmacia), etc. PCR techniques are preferred for site directed mutagenesis (see Higuchi, 1989, "Using PCR to Engineer DNA", in PCR *Technology: Principles and Applications for DNA Amplification*, H. Erlich, ed., Stockton Press, Chapter 6, pp. 61–70).

While a polyglycosyltransferase has been isolated from a bacteria of *Neisseria gonorrhoeae*, polyglycosyltransferases can also be isolated from other bacterial species of Neisseria. Exemplary Neisseria bacterial sources include *N. animalis* (ATCC 19573), *N. canis* (ATCC 14687), *N. cinerea* (ATCC 14685), *N. cuniculi* (ATCC 14688), *N. denitrificans* (ATCC 14686), *N. elongata* (ATCC 25295), *N. elongrata* subsp *glycolytica* (ATCC 29315), *N. elongata* subsp *nitroreducens* (ATCC 49377), *N. flavescens* (ATCC 13115), *N. gonorrhoeae* (ATCC 33084), *N. lactamica* (ATCC 23970), *N. macaca* (ATCC 33926), *N. meningitidis*, *N. mucosa* (ATCC 19695), *N. mucosa* subsp. *heidelbergensis* (ATCC 25998), *N. polysaccharea* (ATCC 43768), *N. sicca* (ATCC 29256) and *N. subflava* (ATCC 49275). Strains assigned American Type Culture Collection (ATCC) accession numbers are available from the ATCC, 1201 Parklawn Drive, Rockville, Md. 20852. In addition polyglycosyltransferases can be isolated from *Branhamella catarrhalis, Haemophilus influenzae, Escherichia coli, Pseudomonas aeruginosa* and *Pseudomonas cepacia.*

Expression of a Polyglycosyltransferase

The gene coding for a polyglycosyltransferase, or a functionally active fragment or other derivative thereof, can be inserted into an appropriate expression vector, i.e., a vector which contains the necessary elements for the transcription and translation of the inserted protein-coding sequence. An expression vector also preferably includes a replication origin. The necessary transcriptional and translational signals can also be supplied by the native polyglycosyltransferase gene and/or its flanking regions. A variety of host-vector systems may be utilized to express the protein-coding sequence. Preferably, however, a bacterial expression system is used to provide for high level expression of the protein with a higher probability of the native conformation. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Preferably, the periplasmic form of the polyglycosyltransferase (containing a signal sequence) is produced for export of the protein to the *Escherichia coli* periplasm or in an expression system based on *Bacillus subtilis*.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

Expression of a nucleic acid sequence encoding a polyglycosyltransferase or peptide fragment may be regulated by a second nucleic acid sequence so that the polyglycosyltransferase or peptide is expressed in a host transformed with the recombinant DNA molecule. For example, expression of a polyglycosyltransferase may be controlled by any promoter/enhancer element known in the art, but these regulatory elements must be functional in the host selected for expression. For expression in bacteria, bacterial promoters are required. Eukaryotic viral or eukaryotic promoters, including tissue specific promoters, are preferred when a vector containing a polyglycosyltransferase gene is injected directly into a subject for transient expression, resulting in heterologous protection against bacterial infection, as described in detail below. Promoters which may be used to control polyglycosyltransferase gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the 0-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; and the like Expression vectors containing polyglycosyltransferase gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a foreign gene inserted in an expression vector can be detected by nucleic acid hybridization using probes comprising sequences that are homologous to an inserted polyglycosyltransferase gene. In the third approach, the recombinant vector/host system can be identified and selected based upon the presence or absence of certain "marker" gene functions (e.g., β-galactosidase activity, PhoA activity, thymidine kinase activity, resistance to antibiotics, transformation phenotype, occlusion body formation in baculovirus, etc.) caused by the insertion of foreign genes in the vector. If the polyglycosyltransferase gene is inserted within the marker gene sequence of the vector, recombinants containing the polyglycosyltransferase insert can be identified by the absence of the marker gene function. In the fourth approach, recombinant expression vectors can be identified by assaying for the activity of the polyglycosyltransferase gene product expressed by the recombinant. Such assays can be based, for example, on the physical or functional properties of the polyglycosyltransferase gene product in in vitro assay systems, e.g., polyglycosyltransferase activity. Once a suitable host system and growth conditions are established, recombinant expression vectors can be propagated and prepared in quantity.

Biosynthesis of Oligosaccharides

The polyglycosyltransferase of the present invention can be used in the biosynthesis of oligosaccharides. The polyglycosyltransferases of the invention are capable of stereospecific conjugation of two specific activated saccharide units to specific acceptor molecules. Such activated saccharides generally consist of uridine or guanosine diphosphate and cytidine monophosphate derivatives of the saccharides, in which the nucleoside mono- and diphosphate serves as a leaving group. Thus, the activated saccharide may be a saccharide-UDP, a saccharide-GDP, or a saccharide-CMP. In specific embodiments, the activated saccharide is UDP-GlcNAC, UDP-GalNAc, or UDP-Gal.

Within the context of the claimed invention, two different saccharide units means saccharides which differ in structure and/or stereochemistry at a position other than $C_1$ and accordingly the pyranose and furanose of the same carbon backbone are considered to be the same saccharide unit, while glucose and galactose (i.e. $C_4$ isomers) are considered different.

A glycosyltransferase typically has a catalytic activity of from about 1 to 250 turnovers/sec in order to be considered to possess a specific glycosyltransferase activity. Accordingly each individual glycosyltransferase activity of the polyglycosyltransferase of the present invention is within the range of from 1 to 250 turnovers/sec, preferably from 5 to 100 turnovers/sec, more preferably from 10 to 30 turnovers/sec.

In addition to absolute glycosyltransferase activity, the polyglycosyltransferases used according to the methods of the invention catalyze a glycidic linkage having a relative activity of from 0.1 to 10 times, preferably from 0.2 to 5 times, more preferably from 0.5 to 2 times and most preferably from 0.8 to 1.5 times, the rate of any one of the other qlycosyltransferase activity identified for that particular glycosyltransferase The term "acceptor moiety" as used herein refers to the molecules to which the polyglycosyltransferase transfers activated sugars.

For the synthesis of an oligosaccharide, a polyglycosyltransferase is contacted with an appropriate activated saccharide and an appropriate acceptor moiety under conditions effective to transfer and covalently bond the saccharide to the acceptor molecule. Conditions of time, temperature, and pH appropriate and optimal for a particular saccharine unit transfer can be determined through routine testing; generally, physiological conditions will be acceptable. Certain co-reagents may also be desirable; for example, it may be more effective to contact the polyglycosyltransferase with the activated saccharide and the acceptor moiety in the presence of a divalent cation.

According to the invention, the polyglycosyltransferase enzymes can be covalently or non-covalently immobilized on a solid phase support such as SEPHADEX, SEPHAROSE, or poly(acrylamide-co-N-acryloxysucciimide) (PAN) resin. A specific reaction can be performed in an isolated reaction solution, with facile separation of the solid phase enzyme from the reaction products. Immobilization of the enzyme also allows for a continuous biosynthetic stream, with the specific polyglycosyltransferases attached to a solid support, with the supports arranged randomly or in distinct zones in the specified order in a column, with passage of the reaction solution through the column and elution of the desired oligosaccharide at the end. An efficient method for attaching the polyglycosyltransferase to a solid support and using such imobilized polyglycosyltransferases is described in U.S. Pat. No. 5,180,674, issued Jan. 19, 1993 to Roth, which is specifically incorporated herein by reference in its entirety.

An oligosaccharide, e.g., a disaccharide, prepared using a polyglycosyltransferase of the present invention, can serve as an acceptor moiety for further synthesis, either using other polyglycosyltransferases of the invention, or glycosyltransferases known in the art (see, e.g., Roth, U.S. Pat. No. 5,180,674).

Alternatively, the polyglycosyltransferases of the present invention can be used to prepare GalNAcβ1-3-Galβ1-4-GlcNAcβ1-3-Galβ1-4-Glc or GalNAcβ1-3-Galβ1-4-GlcNAcβ1-3-Galβ1-4-GlcNAc from lactose or lactosamine respectively, in which a polyglycosyltransferase is used to synthesize both the GlcNAc β1-3-Gal and GalNAc β1-3 Gal linkages.

Accordingly, a method for preparing an oligosaccharide having the structure GalNAcβ1-3-Galβ1-4-GlcNAcβ1-3-Galβ1-4-Glc comprises sequentially performing the steps of:

a) contacting a reaction mixture comprising an activated GlcNAc (such as UDP-GlcNAc) to lactose with a polyglycosyltransferase having an amino acid sequence of SEQ ID NO:3, or a functionally active fragment thereof;

b) contacting a reaction mixture comprising an activated Gal (i.e UDP-Gal) to the acceptor moiety comprising a GlcNAcβ1-3-Galβ1-4-Glc residue in the presence of a β1-4-galactosyltransferase; and c) contacting a reaction mixture comprising an activated GalNAc (i.e UDP-GalNAc) to the acceptor moiety comprising a Galβ1-4-GlcNAcβ1-3-Galβ1-4-Glc residue in the presence of the polyglycosyltransferase of step a).

A suitable β1-4 galactosyltransferase can be isolated from bovine milk.

Oligosaccharide synthesis using a polyglycosyltransferase is generally conducted at a temperature of from 15 to 38° C., preferably from 20 to 25° C. While enzymatic activities of the enzyme are comparable at 25° C. and 37° C., the polyglycosyltransferase stability is greater at 25° C.

In a preferred embodiment polyglycosyltransferase activity is observed in the absence of α-lactalbumin.

In a preferred embodiment polyglycosyltransferase activity is observed at the same pH, more preferably at pH 6.5 to 7.5.

In a preferred embodiment polyglycosyltransferase activities of the enzyme are observed at the same temperature.

Other features of the invention will become apparent in the course of the following descriptions of exemplary embodiments which are given for illustration of the invention and are not intended to be limiting thereof.

EXAMPLE 1

Synthesis of GalNAcβ1-3-Galβ1-4-GlcNAcβ1-3-Galβ1-4-Glc

Lactose was contacted with UDP-N-acetylglucosamine and a β-galactoside β1-3 N-acetylglucosaminyl transferase of SEQ ID NO: 3, in a 0.5 M HEPES buffered aqueous solution at 25° C. The product trisaccharide was then contacted with UDP-Gal and a β-N-acetylglucosaminoside β1-4 Galactosyltransferase isolated from bovine milk, in a 0.05 M HEPES buffered aqueous solution at 37° C. The product tetrasaccharide was then contacted with UDP-N-acetylgalactosamine and a β-galactoside β1-3 N-acetylgalactosaminyl transferase of SEQ ID NO: 3, in a 0.05 M HEPES buffered aqueous solution at 25° C. The title pentasaccharide was isolated by conventional methods.

Obviously, numerous modifications and variations of the present invention are possible in light of the above teachings. It is therefore to be understood that within the scope of the appended claims, the invention may be practiced otherwise than as specifically described therein.

What is claimed is:

1. A method for synthesizing a saccharide composition, comprising:
   (a) contacting a first saccharide donor with a first acceptor moiety in the presence of a polyglycosyltransferase that catalyzes the linkage of a first saccharide to the first acceptor moiety to form an intermediate saccharide composition; and
   (b) contacting a second saccharide donor with the intermediate saccharide composition formed in step (a) or a derivative thereof in the presence of the polyglycosyltransferase that also catalyzes the linkage of a second saccharide to a second acceptor moiety in the intermediate saccharide composition or derivative,
   wherein the relative rate of a first glycosyltransferase activity of the polyglycosyltransferase is 0.8 to 1.5 times the rate of a second glycosyltransferase activity of the polyglycosyltransferase, and wherein the first and second glycosyltransferase activities are each within the range of from 1 to 250 turnovers per second.

2. The method of claim 1, wherein a nucleic acid encoding the polyglycosyltransferase hybridizes to nucleotides 445–1488 of SEQ ID NO:1.

3. The method of claim 1, wherein the polyglycosyltransferase comprises the amino acid sequence of SEQ ID NO:8.

4. The method of claim 2, wherein a nucleic acid encoding the polyglycosyltransferase comprises nucleotides 445–1488 of SEQ ID NO:1.

5. The method of claim 1, wherein the first saccharide is N-acetylglucosamine or N-acetylgalactosamine.

6. The method of claim 1, wherein the second saccharide is N-acetylglucosamnine or N-acetylgalactosamine.

7. The method of claim 1, wherein the intermediate saccharide composition produced in step (a) is contacted with a glycosyltransferase different from the polyglycosyltransferase prior to the reaction of step (b).

8. The method of claim 1, wherein the first and second acceptor moieties have a galactose at the non-reducing terminus.

9. The method of claim 1, wherein the polyglycosyltransferase is isolated from a microorganism selected from the group consisting of *Branhamella catarrhalis, Haemophilus influenzae, Escherichia coli, Pseudomonas aeruginosa* and *Pseudomonas cepacia*.

10. The method of claim 1, wherein the polyglycosyltransferase is isolated from a Neisseria species.

11. The method of claim 1, wherein the polyglycosyltransferase is isolated from a Neisseria species selected from the group consisting of *N. animalis* (ATCC 19573), *N. canis* (ATCC 14687), *N. cinerea* (ATCC 14685), *N. cuniculi* (ATCC 14688), *N. denitrificans* (ATCC 14686), *N. elongata* (ATCC 25295), *N. elongata* subsp. *glycolytica* (ATCC 29315), *N. elongata* subsp. *nitroreducens* (ATCC 49377), *N. flavescens* (ATCC 13115), *N. gonorrhoeae* (ATCC 33084), *N. lactamica* (ATCC 23970), *N. macaca* (ATCC 33926), *N. meningitidis, N. mucosa* (ATCC 19695), *N. mucosa* subsp. *heidelbergensis* (ATCC 25998), *N. polysaccharea* (ATCC 43768), *N. sicca* (ATCC 29256) and *N. subflava* (ATCC 49275).

12. The method of claim 1, wherein the polyglycosyltransferase is isolated from *Neisseria gonorrhoeae*.

13. The method of claim 1, wherein the first saccharide donor or the second saccharide donor is selected from the group consisting of a saccharide-UDP, a saccharide-GDP and a saccharide-CMP.

14. The method of claim 1, wherein the first saccharide donor or the second saccharide donor is UDP-Gal.

15. The method of claim 1, wherein the first saccharide donor or the second saccharide donor is UDP-GlcNAc.

16. The method of claim 1, wherein the first saccharide donor or the second sa e donor is UDP-GalNAc.

17. The method of claim 1, wherein the first and second glycosyltransferase activities are each within the range of from 5 to 100 turnovers per second.

18. The method of claim 1, wherein the first and second glycosyltransferase activities are each within the range of from 10 to 30 turnovers per second.

* * * * *